(12) United States Patent
Maher et al.

(10) Patent No.: US 6,838,680 B2
(45) Date of Patent: *Jan. 4, 2005

(54) MULTIPLEXED FLUORESCENT DETECTION IN MICROFLUIDIC DEVICES

(75) Inventors: Kevin Maher, Woodside, CA (US); Timothy F. Smith, Martinez, CA (US); Torleif O. Bjornson, Gilroy, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 10/202,298

(22) Filed: Jul. 23, 2002

(65) Prior Publication Data

US 2003/0038248 A1 Feb. 27, 2003

Related U.S. Application Data

(63) Continuation-in-part of application No. 10/147,940, filed on May 15, 2002, now Pat. No. 6,614,030, which is a continuation of application No. 09/569,963, filed on May 12, 2000, now Pat. No. 6,399,952
(60) Provisional application No. 60/133,727, filed on May 12, 1999.

(51) Int. Cl.[7] ............................................... G01N 21/64
(52) U.S. Cl. .................. 250/458.1; 250/459.1
(58) Field of Search .................... 250/458.1, 459.1, 250/461.1, 462.2, 574; 356/317, 614

(56) References Cited

U.S. PATENT DOCUMENTS

| 5,296,703 A | 3/1994 | Tsien |
| 5,324,635 A * | 6/1994 | Kawase et al. ............ 435/7.94 |
| 5,459,325 A | 10/1995 | Hueton et al. |
| 5,571,410 A | 11/1996 | Swedberg et al. |
| 5,587,128 A | 12/1996 | Wilding et al. |
| 5,614,726 A | 3/1997 | Kaye et al. |
| 5,630,924 A | 5/1997 | Fuchs et al. |
| 5,730,850 A | 3/1998 | Kambara et al. |
| 5,741,412 A | 4/1998 | Dovichi et al. |
| 5,750,015 A | 5/1998 | Soane et al. |
| 5,833,826 A | 11/1998 | Nordman |
| 5,847,400 A | 12/1998 | Kain et al. |
| 6,614,030 B2 * | 9/2003 | Maher et al. ............ 250/458.1 |
| 2002/0015147 A1 | 2/2002 | Maher et al. |

FOREIGN PATENT DOCUMENTS

| WO | WO 98/49543 | 11/1998 |
| WO | WO 01/20309 A1 | 3/2001 |

OTHER PUBLICATIONS

Huang, C. et al. (1992). "DNA Sequencing Using Capillary Array Electrophoresis," *Analytical Chemistry* 64:2149–2154.

(List continued on next page.)

*Primary Examiner*—Scott J. Sugarman
*Assistant Examiner*—Richard Hanig
(74) *Attorney, Agent, or Firm*—Stephen C. Macevicz

(57) ABSTRACT

An optical detection and orientation device is provided comprising a housing having an excitation light source, an optical element for reflecting the excitation light to an aspherical lens and transmitting light emitted by a fluorophore excited by said excitation light, a focusing lens for focusing the emitted light onto the entry of an optical fiber, which serves as a confocal aperture, and a moveable carrier for accurately moving said housing over a small area in relation to a channel in a microfluidic device. The optical detection and orientation device finds use in detecting fluorophores in the channel during operations involving fluorescent signals.

44 Claims, 17 Drawing Sheets

OTHER PUBLICATIONS

Khandurina, J. et al. (1999). "Microfabricated Poruous Membrane Structure for Sample Concentration and Electrophoretic Analysis," *Analytical Chemistry* 71(9):1815–1819.

Kheterpal, I. et al. (1996). "DNA Sequencing Using a Four–Color Confocal Fluorescence Capillary Array Scanner," *Electrophoresis* 17:1852–1859.

Takahashi, S. et al. (1994). "Multiple Sheath–Flow Gel Capillary–Array Electrophoresis for Multicolor Fluorescent DNA Detection," *Analytical Chemistry* 66(7):1021–1026.

Woolley, A.T. et al. (1994). "Ultra–High–Speed Fragment Separations Using Microfabricated Capillary Electrophoresis Chips," *PNAS USA, Biophysics* 91(24):11348–11352.

* cited by examiner

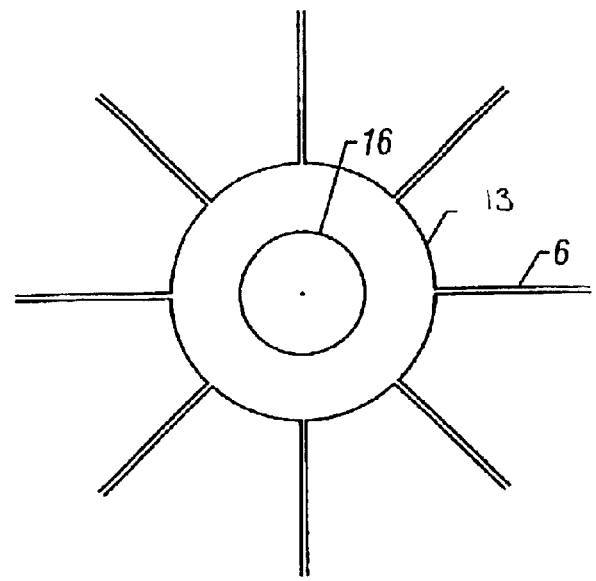
FIG. 13
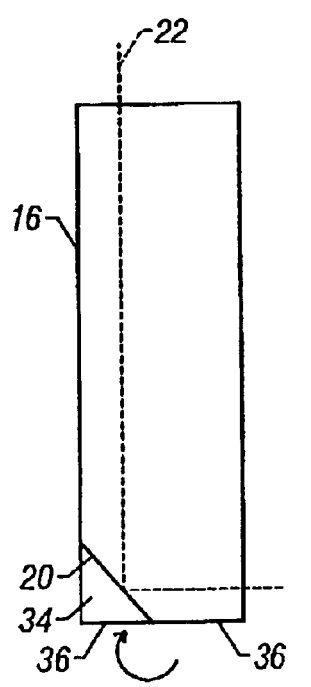 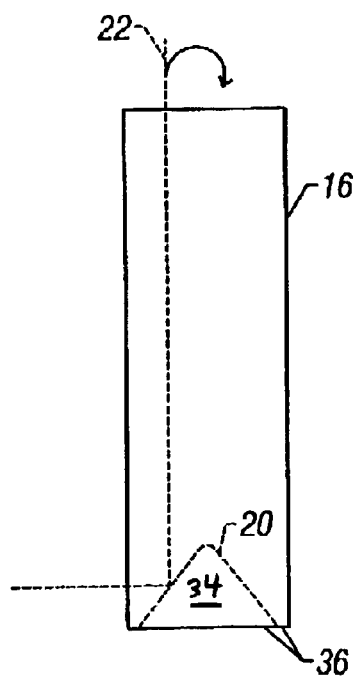
FIG. 14A　　　　FIG. 14B

MULTIPLEXED FLUORESCENT DETECTION IN MICROFLUIDIC DEVICES

CROSS-REFERENCE TO RELATED APPLICATIONS

This application is a continuation-in-part application of U.S. Ser. No. 10/147,940 filed May 15, 2002, now U.S. Pat. No. 6,614,030 which is a continuation application of U.S. Ser. No. 09/569,963 filed May 12, 2000, now U.S. Pat. No. 6,399,952 entitled "Multiplexed Fluorescent Detection in Microfluidic Devices," which claims priority to Provisional Application No. 60/133,727, filed May 12, 1999, each of which is incorporated herein by reference in its entirety.

FIELD OF THE INTENTION

The field of this invention is fluorescent detection in microfluidic arrays.

BACKGROUND OF THE INVENTION

The combination of combinatorial chemistry, sequencing of the genomes of many species and relationships between genotype and physical and biological traits has greatly expanded the need to perform determinations of different events. The multiplicity of new compounds that can be prepared using various forms of combinatorial chemistry and the numerous targets involving wild-type and mutated genes, had extraordinarily increased the number of determinations of interest in developing compounds having biological activity. These compounds include drugs, biocides, pesticide resistance, disease organism resistance and the like. In addition, the interest in discriminating between different genomes, relating specific mutations to phenotypes, defining susceptibilities to various environmental effects in relation to single nucleotide polymorphisms, and identifying the genomes of organisms to provide better defenses against the organisms has expanded the need for rapid, inexpensive devices and methodologies for carrying out these and other determinations.

Recently, microfluidic arrays have been developed which allow for a multiplicity of reservoirs and channels to be associated with a small card or chip, where by using high voltages, various operations can be performed. The arrays provide for individual networks, which exist in combination on a single chip, so that a plurality of determinations may be performed concurrently and/or consecutively. By having channels that have cross-sections in the range of about 500 to 5000 $\mu m^2$, operations can be carried out with very small volumes. In addition, by having very sensitive detection systems, very low concentrations of a detectable label may be employed. This allows for the use of very small samples and small amounts of reagents, which have become increasingly more sophisticated and expensive. Microfluidic arrays offer the promise of more rapid throughput, increasingly smaller times to a determination and increasingly smaller amounts of sample and reagents being required.

The use of microfluidic arrays, however, has its challenges. The microfluidic arrays are desirably made in molded plastic, so as to provide a reduced cost of the chip. By molding the chip and providing for ridges on a mold to form the channels, the channels may not run true and may be displaced from their proper positions, as well as being slightly curved rather than perfectly straight. In addition, the plastic frequently autofluoresces. Since the frequently used label is a fluorescent label, the signal from the label must be able to be distinguished from the autofluorescent signal. There is the problem of how to obtain a reliable fluorescent signal, in effect compromising maximizing the signal from the detectable label while minimizing the background signal.

In addition, the channel walls are not orthogonal to the cover plate, so that the depth of the irradiation may vary, depending upon the site of entry of the excitation beam into the channel. Where the excitation beam encounters the wall, the signal is degraded due to the reduced number of fluorophores which are excited and the excitation of the fluorophores in the wall. Therefore, precise positioning of the excitation beam in the channel is necessary for reproducible and accurate results.

BRIEF DESCRIPTION OF RELATED ART

A number of patents have been published describing systems for detecting fluorescent signals in capillary arrays, such as U.S. Pat. Nos. 5,296,703 and 5,730,850, as well as WO98/49543.

SUMMARY OF THE INVENTION

An optical fluorescence detection system is provided for use with microfluidic arrays. The detection and orientation system comprises an optical train for receiving and processing light from a source of light and directing the light onto a microfluidic channel in a solid substrate. The optical train is moved across the surface of the solid substrate, crossing the channel and receiving the light emanating from the solid substrate. The optical train directs and processes the light from the solid substrate surface and directs the light to a detector. The signal from the detector is received by a data analyzer, which analyzes the signals and directs the optical train to the center of the channel in relation to the observed signals from the bulk material of the solid substrate, the edges of the channel and from the channel. Fluorescent components in the channel are detected by the fluorescence produced by the excitation light, where the emitted light is processed by the optical train and analyzed for the presence of fluorescence in the channel resulting from the fluorescent components in the channel, correcting for any fluorescence from the solid substrate.

An optical receiver may collect light emanating from a detection volume or segment of the microchannel. The optical receiver may transfer the emanating light to at least one detector. The light emanating from the detection volume may include but is not limited to one or more of the following: light emitting from fluorescent sample material in the detection volume; light emitting or reflecting from the walls of the microchannel which define the detection volume; and other light arising from that region. Light may also be scattered off the channel walls, the media in the channel, or the card material.

The light source may be part of the moving optical train. Also, the light source may be divorced or separated from the moving optical train.

The optical fluorescence detection system employs a plurality of miniaturized confocal microscope systems aligned in orientation with a plurality of channels of a microfluidic array. The systems are mounted on a movable support for alignment with sets of channels. The supports may be mounted on a carriage for alignment with different sets of channels. An irradiation unit comprises a source of light and processing means, such as lenses, dichroic mirrors, filters, gratings or the like, to reject light outside the wavelength range of interest. A single light source may be used and the beam split into a plurality of optical fibers for individual distribution of beamlets for channel irradiation. Similarly, the individual signals from each of the channels is directed by individual optical fibers to a common detector. Alternatively, individual light sources may be used for each confocal microscope system, such as LEDs or laser diodes.

The light source may be a multiple-wavelength light source. It may emit light at multiple wavelengths or it may selectively emit light at different wavelengths. An example of a multiple-wavelength light source is a mixed-gas laser. Light may be emitted at a wide variety of wavelengths including, e.g., 488, 532, and 633 nm.

Also, the light source may be adapted to deliver an expanded-beam having a diameter in the range of 2 to 50 mm. The light source may also be configured to deliver a fine or collimated beam having a diameter in the range of 0.1 to 2 mm.

The methodology allows for an accurate, reproducible determination of a fluorescent signal from each of the channels. In order to achieve the desired sensitivity for detection, the center of each channel is determined, either when the channel is empty (air) or when a liquid is present, usually containing a fluorescent dye. Depending upon the degree of autofluorescence of the microfluidic array substrate, the optical system may look at fluorescent light, where there is sufficient autofluorescence to provide a detectable signal or scattered light, usually where the autofluorescence is low. In the case of scattered or reflected light, one would be detecting a different wavelength from the light, which would result from autofluorescence.

There are two different forms of delivering excitation: single mode fiber delivery or no fiber, where a laser and splitting may be done by discrete mirrors or a diffraction optical element; or multi-mode fiber delivery, where either a lamp or a laser may be used and splitting is done by homogenizing the laser or lamp light and then splitting using a multi-mode fiber array. An example of a light source is a laser having a wavelength in the range of about 250 to 800 nm. Also, the laser may emit light at a wavelength of 488, 532, and 633 nm.

The optical detection and orientation system can also have multiple light sources, each emitting light at a different wavelength. Examples of light sources include but are not limited to a lamp, laser, LED, or laser diode. In one variation, at least one light source emits a wavelength in the range of 250 to 800 nm.

Depending upon the source of light, such as a laser, a filter may be used to attenuate the intensity of the light to minimize photobleaching and photodestruction of the fluorescent labels. The light is then split into a plurality of rays or beamlets by a diffractive optical element, a combination of beam splitter elements, such as discrete mirrors, or other means, such as discrete beam splitters and fiber optic arrays. Each of the resulting beams is then directed to the individual confocal microscope associated with the channels. Either a single mode or multimode fiber may be employed, where one may use a multimode fiber optic array to split the illumination into N beamlets, where N is the number of optical trains to be illuminated. The fiber will generally have a diameter in the range of about 25 to 75 $\mu$m, particularly about 50 $\mu$m and a length in the range of about 1 to 1,000 mm.

The confocal housing can be very compact, where the portion enclosing the optical train, usually in conjunction with other enclosed areas associated with the optical fibers and attachment to the orienting system, generally having a total volume of about 0.5 to $4 \times 10^4$ mm$^3$, with a cross-section in the range of 200 to 2000 mm$^2$ and a height in the range of about 25 to 200 mm. Each confocal microscope housing receives an individual light source optical fiber, with the fiber oriented such that the output face is normal to the optical axis of the housing and the light emerging is coincident with the optical axis. An optical system, usually involving a collimating lens and objective lens, are positioned such that they focus the light from the fiber to a small spot. These lenses are usually aspherical with a single element. They are designed to be small, yet still offer diffraction limited performance.

Instead of having the optical fiber positioned at the optical axis, the chief ray from the optical fiber may be directed through a collimating lens, which is outside the optical axis and collimates the light and directs the light to a dichroic mirror. The dichroic mirror directs the chief ray along the optical axis of the housing. The chief ray is focused by means of a lens with a high numerical aperture, generally in the range of about 0.25 to 0.75. The irradiation spot size may have a diameter of about 6 to 10 $\mu$m, while the collection area may be about 200 to 600 $\mu$m$^2$. The excitation light will excite fluorophores present in the channel at the detection site and the fluorescent light emitted from the channel can be collected by the high numerical aperture lens. When a collimating lens is used, the light may be directed past the collimating lens. By proper positioning and design of the collimating lens, photon losses due to obscuration by the collimating lens can be minimized. Where the dichroic mirror is employed, the mirror may be substantially transparent in the wavelength range of interest and the light beam focused by the focusing lens can pass through the dichroic mirror. After passing through the dichroic mirror or past the collimating lens, the light beam will usually be filtered to remove light outside the wavelength range of interest and be refocused onto a plane that contains the entrance aperture or core of a multimode optical fiber. The emission fiber will have substantially the same dimensions as the excitation fiber. The aperture acts as the confocal aperture for the confocal assembly, although there are other ways to provide the confocal pinhole, such as avalanche photodiodes, and other detectors. The emission beam is received and directed by the emission optical fiber to a detector. Various detectors may be employed which have the appropriate sensitivity, such as photomultiplier tubes (PMTs), charged coupled detectors (CCDs), avalanche photodiodes, etc. The signal may then be processed to provide the level of emission obtained from the channel and relate this intensity to the amount of fluorophore in the channel. Since the amount of fluorophore will relate to an event of interest, it may serve to identify the nature of the sample.

In some situations one will be interested in signals coming from different fluorophores having different wavelength ranges. The emission light beam may be split into the number of different wavelengths of interest, using filters, dichroic mirrors, prisms and the like. Various commercial systems are available for this purpose, such as prisms, beam splitter mirrors, etc. The subject assembly with the fiber preserves the laser light source mode and profile and assures optimal focusing of the ray on the sample by the confocal microscope assembly.

The housings may be used individually, but will usually be used in combination to read a plurality of channels at detection sites. The individual housings are mounted on a support, which will usually be mobile to allow for the support to move and reorient the housings in relation to different sets of channels. The movable optical train may be adapted to scan across one or more channels. For example, with 8 housings, one may read 8 channels, and by being able to move the support one may read different groups of 8 channels, so that with 12 readings, one could read the samples from a 96 assay plate pattern. By having 12 housings or more, usually not more than about 96 housings, one could read a large number of samples quickly, since an individual reading would take less than a few seconds and the movement of the support would be automated and the entire set of readings would be performed in less than about a minute. The support allows for movement of the housings, so as to orient the beam to substantially the center of the channel. Various methods may be used for controlling the movement of the housings, including mechanical, electromechanical, electromagnetic, and the like. The different methods may involve anchoring the housing to an arm mounted on a pivot rod, where the arm is restrained in one direction and urged in the opposite direction, a voice coil actuator, where the lever arm extends into the center of the coil. By using a control rocker arm which is cam operated, or a movable support which moves in a plane, the housing can be moved up to a distance of about 10 $\mu$m to 50 mm, usually 500 $\mu$m to 5 mm, from a central point. Where the bulk material of the microfluidic chip is autofluorescence, the presence of the channel is determined by detecting the autofluorescence as one moves the illumination through a predetermined distance. With both autofluorescence and light scatter, where the bulk material is not significantly autofluorescent, there will be a channel signature as depicted in FIG. 9, showing the change in autofluorescent signal as the illumination traverses the channel.

Additionally, channel finding algorithms are described in U.S. patent application Ser. No. 09/859,749 filed May 17, 2001 and entitled "Optical Alignment in Capillary Detection Using Capillary Wall Scatter" which is hereby incorporated by reference.

The control arm is rigidly joined to the housing. The control arm is pivotally mounted on a bearing, so as to be able to move in a small arc about the channel. The arm can be actuated to scan the surface of the microfluidic chip about this arc, using the optical system for fluorescent detection to determine the site of the channel. Various actuators may be used for moving the arm and the housing, where the movement may be accelerated and decelerated as it passes through the arc. The observed autofluorescence is transmitted to the detector and the signals analyzed to determine the site of the channel. Once the borders of the channel have been determined, the housing and its optical axis may be oriented to be substantially above the center of the channel.

The length of the housing and lever arm may be relatively short, generally when measured from the axis of the bearing to the lens at the end of the housing adjacent to the microfluidic device, being in the range of 50 to 150 mm. Movement of the housing may be controlled to at least steps of about 0.01 $\mu$m, generally in the range of about 0.1 to 10 $\mu$m. Instead of using a mechanical arm, one may use various electromagnetic assemblies to control the movement of the housing in relation to an optical signal. By having opposing electromagnets or a single electromagnet with an opposing force, the flux of the electromagnet is controlled by a computer, which relates the position of the housing to the change in signal as the housing traverses the channel area. Alternatively, one may use a motor and guide shaft for moving the housing, which allows the housing to traverse the channel area in a plane parallel to the surface of the chip.

Desirably one uses a single light source for a plurality of optical systems. The light from the single source is directed to a beam divider, such as a diffractive optical element or a system of beam splitters. Each of the beamlets is directed to an optical fiber, which conducts the light to the optical system. While the light may be split into any number of rays, usually the total number of rays will typically not exceed 96, usually not exceed 64, more usually not exceed 32 and may be as few as 4, preferably from about 8 to 24. Each light ray may be separated by an angle $\theta$ in a linear array, but a two dimensional array may also be formed with the appropriate angle between rays. Each ray has similar propagation parameters as the input beam. In particular, the divergence, and transverse intensity profile are preserved. When the transverse intensity profile of the light source is the "Gaussian" or $TEM_{00}$, then each ray will preserve this profile. This profile permits optimal focusing. Each ray is propagated a sufficient distance to provide separation and a distinct position. The distance will generally be at least 1 mm, usually in the range of about 1 to 1,000 mm. Individual lenses, such as aspherical lenses, achromatic doublets, etc., focus each ray into a single mode optical fiber. Each fiber is connected to one of the confocal microscope assemblies, which is associated with each channel.

The microfluidic array will generally be in a solid substrate, which may be an inflexible substrate or a flexible substrate, such as a film. Examples of solid substrates may include glass, plastic, and silicon. For examples of microfluidic devices, see, for example, U.S. Pat. No. 5,750,015. If flexible, it will usually be supported and oriented in conjunction with a rigid support. The channels comprising the detection site will generally have a depth of about 10 to 200 $\mu$m and a width at the opening of the channel in the range of about 1 to 500 $\mu$m, usually 10 to 200 $\mu$m. The channels may be parallel or in various arrays, where the inlet ports may be oriented in relation to a 96 or higher microtiter well plate, so that samples from the wells may be directly introduced into the port and microfluidic network. Depending on the purpose of the chip and the pattern of channels, whether the channels are straight, curved or tortuous, the chip may be only 1 or 2 cm long or 50 cm long, generally being from about 2 to 20 cm long, frequently 12.8 cm long. The width may vary with the number and pattern of channels, generally being at least about 1 cm, more usually at least about 2 cm and may be 50 cm wide, frequently about 8.5 cm wide. The chips will have inlet and outlet ports, usually reservoirs for buffer and waste, which are connected to the channels and there may be additional channels connected to the main channel for transferring sample, reagents, etc., to the main channel. Electrodes will be provided for the channels, where the electrodes may be part of the chip, painted with electroconductive paint or metal plated on the chip, or electrodes may be provided for introduction into the reservoirs or channels by an external device. The spacing between the channels will usually be at least about 0.25 mm, more usually at least about 1 mm, at the detection site. Since the channels may take many courses and shapes, the distance between two adjacent channels may vary.

In order to make a series of determinations in the chip, the chip is introduced into a module or group of modules, which include the movable support. The chip will be indexed in relation to the support, so that the channels will be substantially oriented in relation to the optical axis of the associated housings. The module may also include electrodes or connectors to electrodes, which are part of the chip, containers or other instrumentality, e.g. syringes, capillaries, etc., which can serve as sources of reagents, sample, and the like, which provide for fluid transfer through the ports in the chip, electrical connections between the fluorescent detectors and a data analysis system, and the like. The various modules are combined, so as to receive the chip and orient the chip in relation to the various components, which interact with the chip. Indexing may be provided on the chip, so as to be locked in a predetermined position in relation to the module and the support. Prior to initiating operation in the channel, the housings are oriented in relation to the centers of the channels. Each of the housings is individually moved across the plane of the microfluidic chip intersecting the channel at the detection zone. Depending upon the level of autofluorescence of the composition of the substrate, autofluorescence or scattered light may be read. Where there is significant autofluorescence, autofluorescence or scattered light may be detected and read. Where the autofluorescence signal is low, scattered light can be read.

Where scattered light is being detected, the scatter may be different at the edges of the channel, as compared to the scatter from the channel. By observing the change in the scattered light, as the housing moves across the plane of the microfluidic chip, one can detect the transition from the edges of the channel to the channel and select the center as equally distant from the edges.

Once the housings are fixed in registry with the channel, the orientation process need not be repeated in relation to the channel and optical housing and numerous readings may be taken. One may then perform various operations, where a fluorophore label is brought to the detection site. The detection of the fluorophore label may be as a result of a competition assay, nucleic acid sequencing, immunoassays, etc.

BRIEF DESCRIPTION OF THE FIGURES

FIG. 13 shows an alternate configuration for a portion of a microfluidic device;

FIGS. 14A and 14B show prism configurations complimentary to the device shown in FIG. 13;

DETAILED DESCRIPTION OF THE INVENTION

Figure 1:
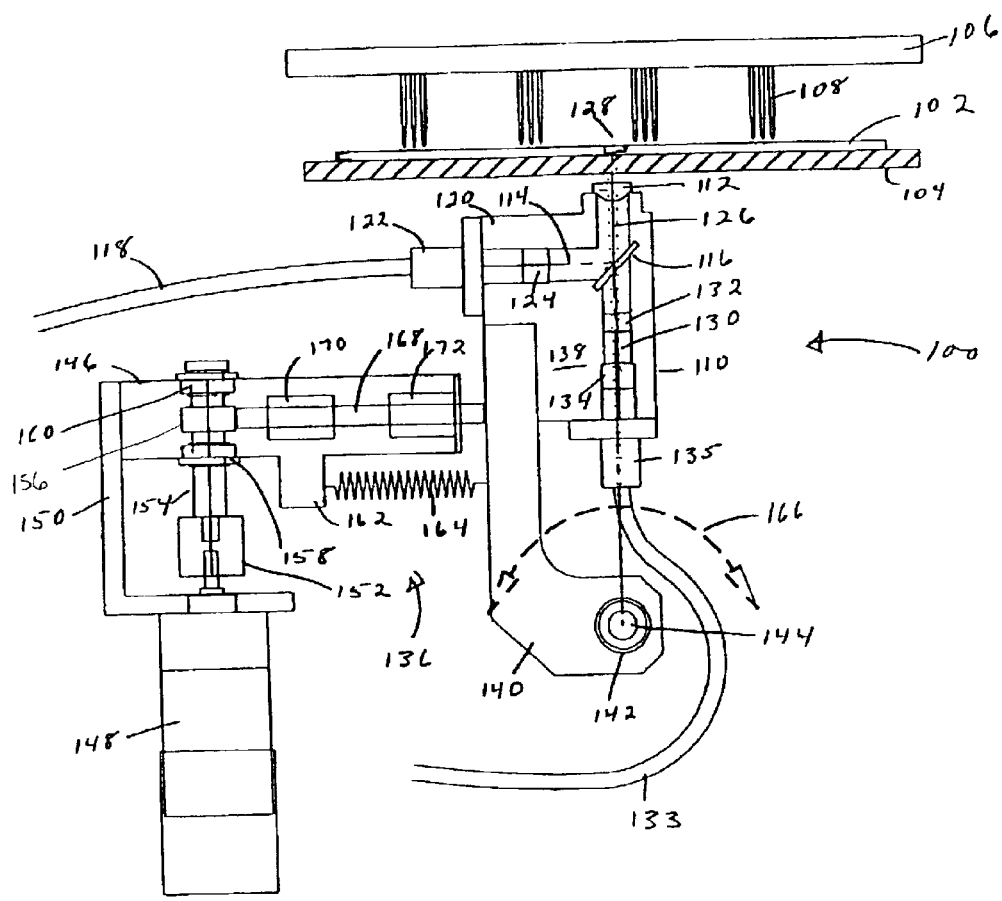
FIG. 1 is an elevational side view of an optical detection system.

For further understanding of the invention, the drawings will now be considered. In FIG. 1 is depicted a detection station 100. In conjunction with the detection station is a microfluidic chip 102, held in position by a quartz plate 104. The quartz plate may be part of a vacuum chuck, not shown, whereby the microfluidic chip 102 is held in fixed registry in relation to the detection station 100. Other ways of maintaining the microfluidic chip in place include gravity, force pins, pressure, clips, reversible adhesives, etc. Also depicted is an electrode lid 106 with electrodes 108, where the electrodes 108 can extend into ports of the microfluidic chip 102, during operation of electrokinetic processes. As described above, the microfluidic chip 102 may have a plurality of channels, where the system for only one channel is shown. The detection station has optical housing 110, which is a small tubular housing, which may be made of any convenient material, e.g., plastic, aluminum, steel, etc., and will desirably have the minimal dimensions necessary for housing the various components of the optical system. The optical system, to the extent permissible, can employ miniaturized optical elements, such as diffractive optical elements, DOEs. A single DOE may serve a plurality of functions, such as acting as a lens, mirror and/or grating, where the component will be about 3 mm×3 mm. The optical system includes an aspherical lens 112 at one end of the housing in apposition to the channel in the microfluidic chip, which aspheric lens 112 directs the excitation beam to the center of the channel after appropriate orientation, as described below. An excitation light beam 114 is directed to dichroic mirror 116 or equivalent optical element by means of optical fiber connected to arm 120 of housing 110 by means of coupler 122. Light beam 114 passes through a lens 124, which serves to collect the divergent light from the fiber. The excitation beam 114 is then reflected by dichroic mirror 116, which reflects light of the excitation wavelength of interest and allows light outside the reflective wavelength to pass through the dichroic mirror. The internal walls and all supporting elements will desirably be black, so as to maximize scattered light absorption. The reflected light beam 126 is focused by aspherical lens 112 and forms a sharp small beam, which passes through the support plate 104 into channel 128. When fluorophore is in the channel 128, the fluorophores will be excited and emit light, which will exit the channel 128 and be collected by the aspherical lens 112. The emission beam may pass through the dichroic mirror 116, filter 132 to reject light outside the wavelength range of interest and lens 134 which focuses the light beam 130 on the entry of collection optical fiber 132. The optical fiber is attached to the housing 110 by means of coupler. The collection optical fiber 132 transfers the photons to a detector, not shown.

The housing 110 is affixed to the orientation device 136 by means of flange 138. Flange 138 is bonded to and connects together as a movable unit housing 110, arm 120 and lever 140. Lever 140 is rotatably mounted on bearing 142, which is supported by axle 144. The orientation device 136 comprises a tubular casing 146, which is fixedly attached to the encoder unit 148 by L-bar 150. The casing 146 and motor unit 148 are held in fixed relationship, so that movement of the lever arm 140 can be accurately controlled and the position of the lever arm 140 and in this way the housing 110 readily determined. The encoder 148 is connected by connector 152 to the rod 154 on which cam 156 is fixedly mounted. Rod 154 passes through bearings 158 and 160, which are set in tubular casing 146, so as to maintain rod 154 in place and allow for rotation of cam 156 from a fixed axis of rotation. The tubular housing 146 has a fin 162 to which one end of a spring 164 is attached, being attached at the other end to lever arm 140. The spring 164 restrains lever arm 140 and urges the arm 140 in the direction of the fin 162 or in the counter-clockwise direction as indicated by broken line 166. Bar 168 is supported by bushings 170 and 172 and its length provides for a tight fit between the cam 156 and the contact position on lever arm 140. Therefore, the distance between the surface of the cam 156 on which the bar 168 is displaced and the lever arm 140 remains constant. As the cam 156 rotates, the bar 168 is extended or retracted in relation to the rod 154 on which the cam is journaled. As the lever arm 140 responds to the movement of the bar 168, the optical system in housing 110 scans the surface for the fluorescence being emitted. The light source may be part of the moving optical train. Also, the light source may be divorced or separated from the moving optical train. As indicated previously, there may be a substantial drop at the borders of the channel 128 in the microfluidic chip 102. By knowing the position of the borders and the distance between the borders, the encoder can be controlled to move the bar 168 to center the housing 110 over the center of the channel 128. Once the housing is centered over the channel, the electrokinetic determination may be made and the change in fluorescence monitored in the channel 128, with the change in signal resulting from the change in fluorescence intensity directed by collection fiber 132 to a data collection and analysis device, not shown.

The microfluidic chip may be oriented so as to have a single channel within the confines of the width of a single housing so that the determination of the channel center is orthogonal to the channel. Alternatively, the channel may be at an angle to the path of the housing, so that the measurements are at an angle to the channel boundaries, still allowing for the center to be determined. Instead of having the housings in a row, the housings may be organized in any manner which allows them to determine the boundaries of the channel at the detection site, such as forming an arc, an equally spaced apart array with a number of columns and rows, or other pattern in relation to the pattern of the detection sites of the channels to be monitored.

The optical detection and orientation system may have multiple light sources each emitting light at a different wavelength. Also, the optical detection and orientation system may have a multiple-wavelength light source, which may selectively emit light at different wavelengths. Examples of light sources may include, but are not limited to, the following: multiple-wavelength lasers, such as mixed-gas (argon and krypton) ion lasers, dye or multiple-dye lasers (pumped by either flashlamp or laser); an optical parametric oscillator (OPO) that is pumped by any uv laser, such as a frequency-quadrupled Nd:YAG laser; and pulsed xenon short-arc lamp in cooperation with a rapidly tunable optical filter, such as a small monochromator or a set of interference filters.

Also, the light source may be adapted to deliver an expanded-beam having a diameter in the range of 2 to 50 mm. The light source may also be configured to deliver a fine or collimated beam having a diameter in the range of 0.1 to 2 mm.

Figure 2:
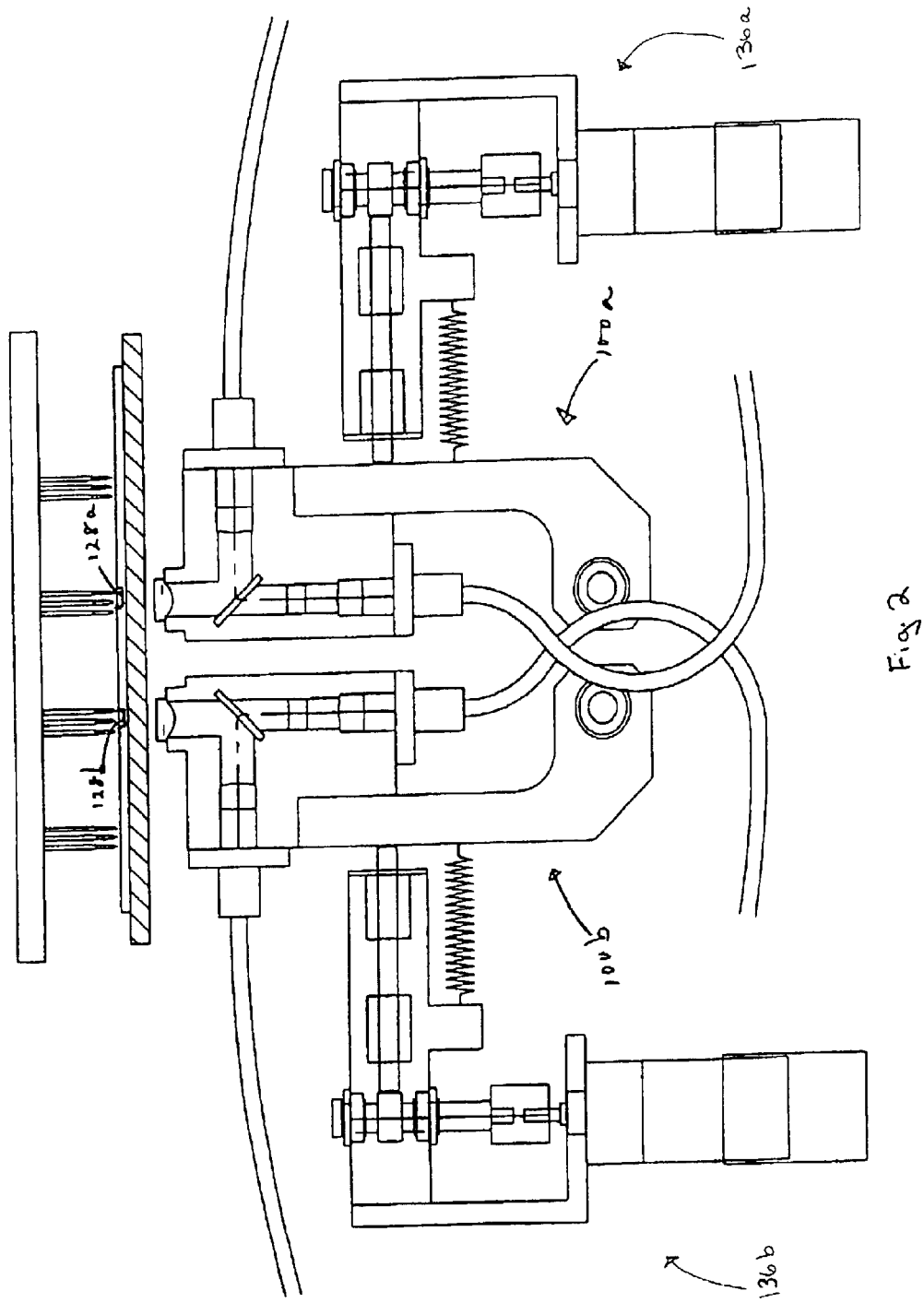
FIG. 2 is an elevational side view of a pair of optical detections systems.

In FIG. 2 is shown an analogous device as depicted in FIG. 1, except that there are two complete units, which are confronting and monitor two different channels. In this arrangement, one has two rows of devices. Since all of the parts are the same, the same numbering has been used to indicate the different components. The two detection stations 100a and 100b confront each other over channels 128a and 128b. Each of the detection stations 100a and 100b move independently of each other having their own orientation devices 136a and 136b, respectively. By having two sets of optical detection stations, one doubles the number of readings that can be performed at the same time. Where the channels are orientated properly, the two rows of optical detection stations monitor two sets of channels and provide data more rapidly.

Figure 3:
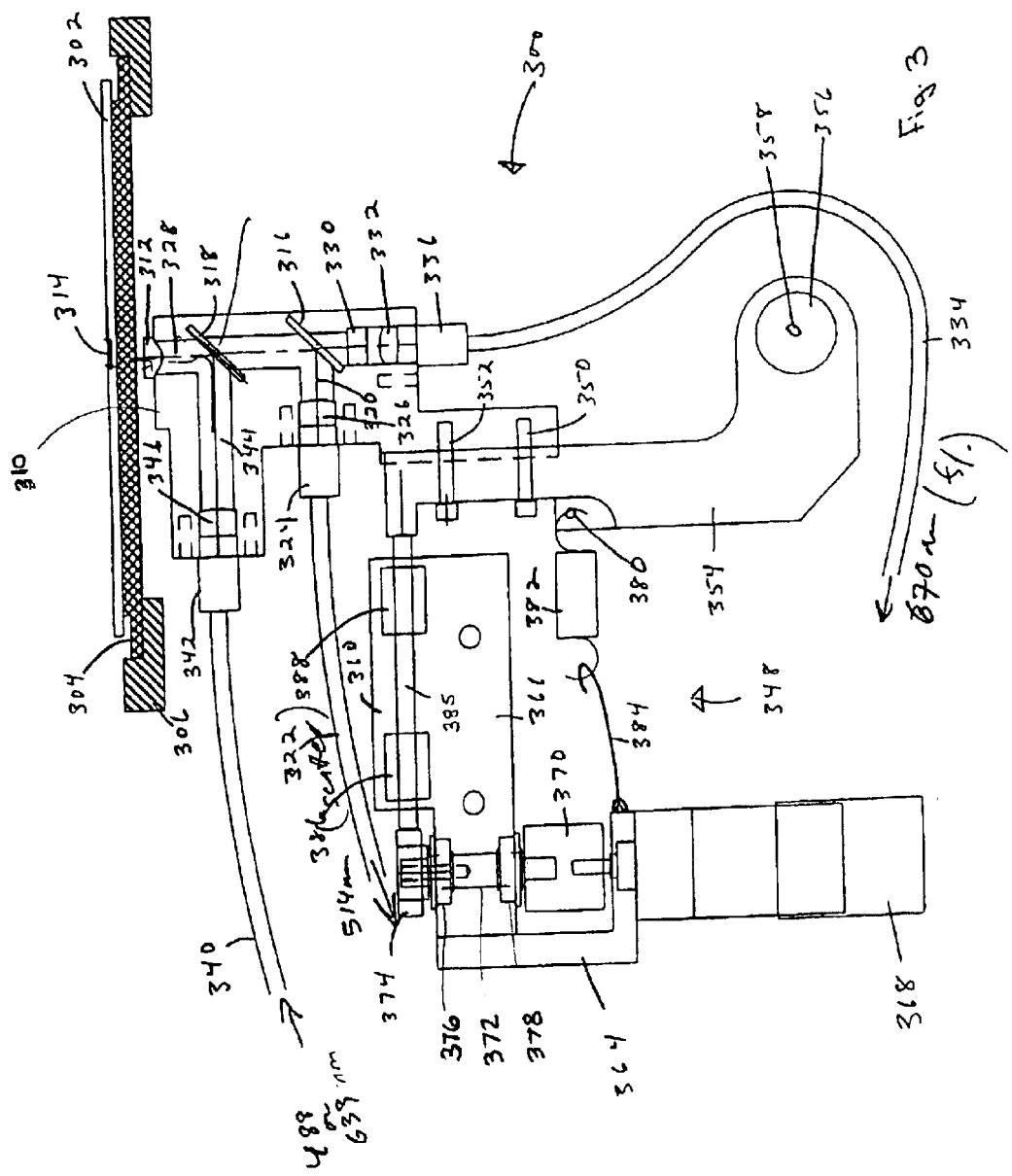
FIG. 3 is an elevational side view of an alternative optical detection system.

In FIG. 3, a modified structure is provided, which can be used in two ways: in a first way, it allows for identifying fluorophores having different absorption wavelengths; and in a second way, it employs a single wavelength but uses a different path for detection of scatter from the microfluidic chip. The figure also provides a different mechanical structure for the orientation device. The optical detection device 300 has microfluidic chip 302 held in position by glass plate 304 in vacuum chuck 306. The microfluidic chip 302 is held in fixed registry in relation to the detection station 300. An electrode lid or other electrode source, not shown, is provided for the voltage across the channels of the microfluidic chip 302. The detection station has optical station 310, which is a small tubular housing, which will be at least about 3 mm OD, more usually, at least 5 mm OD and usually not more than about 15 mm OD, more usually not more than about 10 mm OD. Desirably, the spacing center-to-center of the housings in a row will be from about 6 to 12 mm, more particularly 8 to 10 mm. The housing may be made of any convenient material, metal or plastic, with the minimal dimensions required containing the optical train and providing the desired specifications. The optical system, to the extent permissible, may employ miniaturized optical elements, such as diffractive optical elements. The optical system includes an aspherical lens 312 at one end of the housing in apposition to the channel 314 in the microfluidic chip 302. The aspherical lens 312 directs the excitation beam to the center of the channel after appropriate orientation. It also serves to transmit a small light beam for detection of the boundaries of the channel 314. The housing has two dichroic mirrors, an upper dichroic mirror 316 and a lower dichroic mirror 318. The two mirrors find use for using two different wavelengths for excitation of fluorophores. An upper excitation light beam 320 is directed to upper dichroic mirror 316 or equivalent optical element by optical fiber 322 connected to housing 310 by means of coupler 324. Light beam 320 passes through a bandpass filter 326, which rejects light out of a first wavelength range of interest. The excitation light beam 320 is then reflected by dichroic mirror 316, which reflects light within the wavelength light of interest and allows emitted light of the wavelength of interest to pass. The internal walls and supporting elements are desirably black. The reflected light beam 328 is focused by aspherical lens 312 to a sharp small beam, desirably in the range of about 5 to 25 µm. The irradiation beam excites fluorophores in the channel at the detection site and light is emitted. By having a beam of about 10 µm in diameter, with a channel of about 50 µm in width and 100 µm in depth, the volume which is irradiated is about 4 pl. For a 50 pM concentration of fluorophores, the number of molecules which are irradiated are about 118. The emitted light passes through dichroic mirrors 318 and 316 through filter 330, which rejects light outside of the wavelengths of the two different fluorophores and is focused by objective lens on the entry of collection optical fiber attached to housing 310 by coupler. The entry of the collection optical fiber 334 serves as the confocal aperture. In analogous manner lower optical fiber 340 is connected to housing 310 through coupler 342 and directs a light beam 344 of a different wavelength from light beam 320 through bandpass filter 346. The light beam 344 acts analogously to light beam 320, being reflected by dichroic mirror 318 into the channel 314, where fluorescent light is emitted, collected and focused by aspherical lens 312 and directed through both dichroic mirrors 318 and 316 to the confocal aperture provided by the entry to multimode optical fiber 334.

For determining the center of the channel 314, an orientation mechanism 348 is provided, which is substantially the same as the orientation mechanism of FIG. 1. The housing 310 is affixed to the orientation device 348 by means of bolts 350 and 352. The bolts extend through lever arm 354. In this way housing 310 is secured to and connects together as a movable unit housing 310 and lever 354. Lever 354 is rotatably mounted on bearing 356, which is supported by axle 358. The orientation device 348 comprises a tubular casing 360, which is fixedly attached to the encoder unit 368 by L-bar 364 and flange 366. The casing 360 and encoder unit 368 are held in fixed relationship, so that movement of the lever arm 354 can be accurately controlled and the position of the lever arm 354, and in this way the housing 310, can be readily determined. The encoder 368 is connected by connector 370 to the rod 372 on which cam 374 is fixedly mounted. Rod 372 passes through bearings 376 and 378, which are set in flange 366, so as to maintain rod 372 in place and allow for rotation of cam 374 from a fixed axis of rotation. Lever arm 354 has pin 380 to which spring 382 is attached, where the other end of spring 382 is affixed to a hook 384 attached to L-bar 364. The spring 382 restrains lever arm 354 and urges the arm 354 in the direction of the L-bar. Bar 385 is supported by bushings 386 and 388 and its length provides for a tight fit between the cam 374 and the contact position on lever arm 354. Therefore, the distance between the surface of the cam 374 on which the bar 385 is displaced and the lever arm 354 remains constant. As the cam 374 rotates, the bar 385 is extended or retracted in relation to the rod 372 on which the cam is journaled. As the lever arm 354 responds to the movement of the bar 385, the optical system in housing 310 scans the surface for the fluorescence being emitted. As indicated previously, there may be a substantial drop at the borders of the channel 314 in the microfluidic chip 302. By knowing the position of the borders and the distance between the borders, the encoder can be controlled to move the bar 385 to center the housing 310 over the center of the channel 314. Once the housing is centered over the channel, the electrokinetic determination may be made and the change in fluorescence monitored in the channel 314, with the change in signal resulting from the change in fluorescence intensity directed by collection fiber 334 to a data collection and analysis device, not shown.

In the second use of the device, optical fiber 340 provides the excitation light, which is reflected to the microfluidic chip 302. The dichroic mirror 316 collects the scatter light and transmits that light to a collection optical fiber 322. Both dichroic mirrors 316 and 318 are transparent to the fluorescent signal emitted from the channel 314, which fluorescent light is transmitted to optical fiber 334 for processing by a data processor.

In the next series of figures, the common elements to the figures will not be repeated. They provide an environment for the different devices for moving the housing to identify the site of the channel center.

Figure 4:
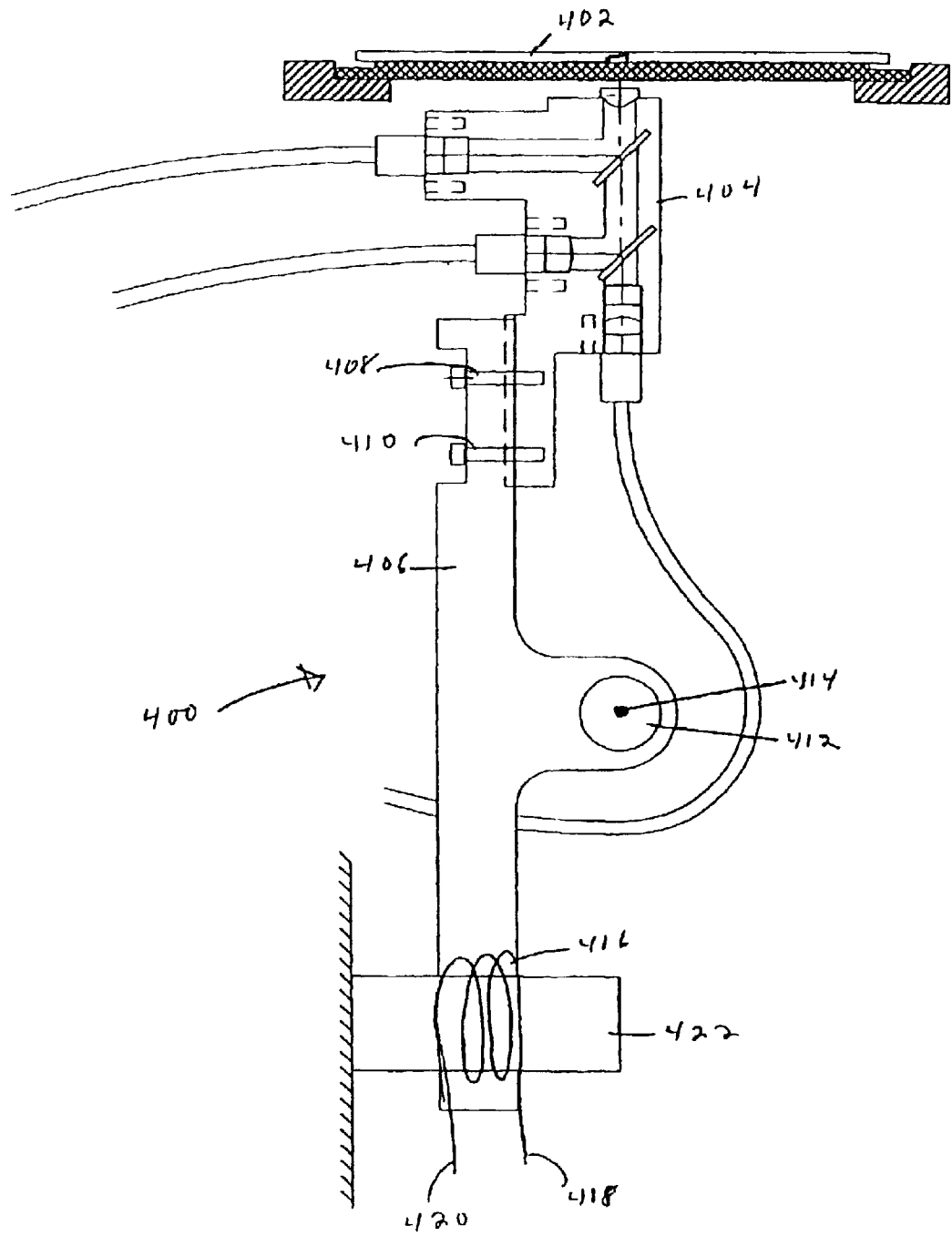
FIG. 4 is an elevational view of an alternative embodiment using an electromagnetic actuator for orienting the optical detection system.

In FIG. 4, the device 400 is associated with microfluidic chip 402, and has optical station 404, which includes the same optics as described in FIG. 3 for housing 310. Optical station 404 is fastened to arm 406 by set screws 408 and 410. Arm 406 has bearing 412, which is mounted on pivot rod 414. Arm 406 terminates in electrical coil 416, which has leads 418 and 420. A magnetic bar 422 extends through coil 420. The leads are connected to a source of dc current, not shown, which is controlled by a data analyzer, also not shown. The signal from optical system 404 is sent to the data analyzer, which detects the change in signal as the housing traverses the plane of the microfluidic chip 402 and identifies the center of the channel. The data analyzer changes the current in the coil to move the arm 406 to scan the surface of the microfluidic chip 402. When the center of the channel is identified, the data analyzer fixes the position of the housing to direct the excitation light to the center of the channel.

Figure 5:
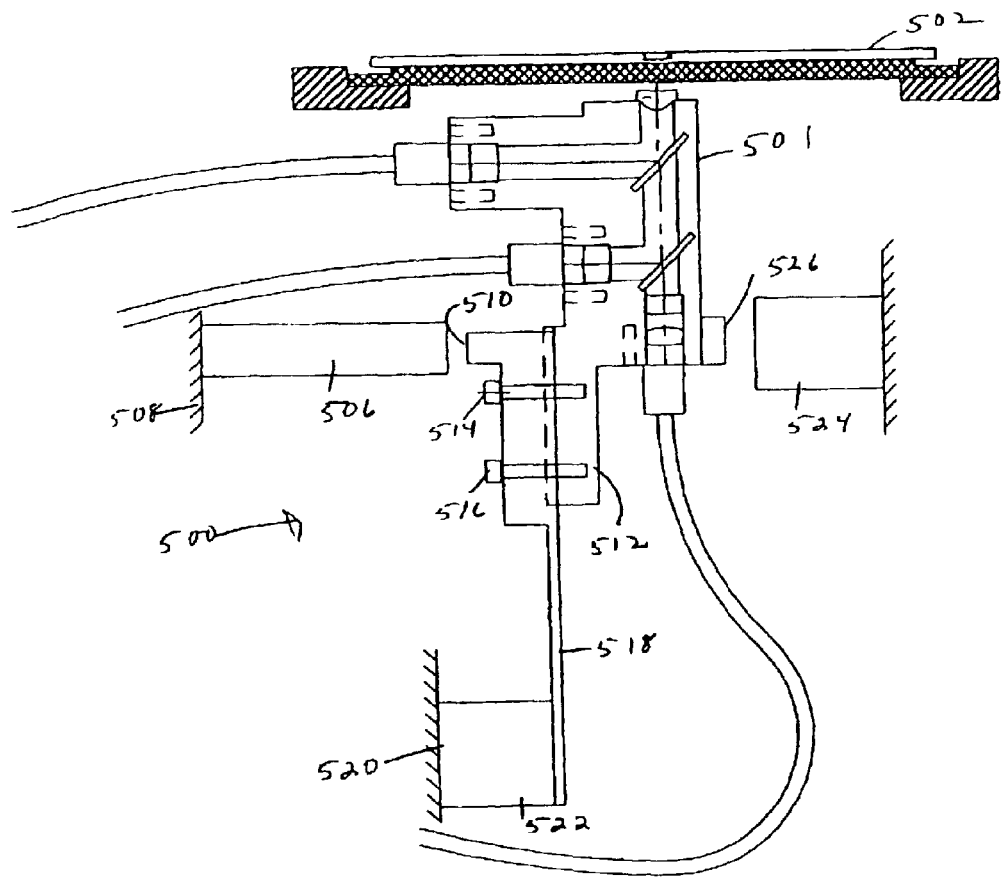
FIG. 5 is an elevational view of an alternative embodiment using a second manner of using an electromagnetic actuator for orienting the optical detection system.

In FIG. 5, an alternative electromagnetic device is employed. The device 500 is associated with microfluidic chip 502 and has optical station 504, which includes the same optics as described in FIG. 3 for housing 310. An electromagnetic actuator 506 rigidly affixed to a support 508 and confronts iron surface 510. The housing 504 is attached at flange 512 by means of bolts 514 and 516 to a flexible pivot arm 518 which is affixed to support 520 by bar 522. When the electromagnetic acuator 506 is activated by applying a current to the electromagnetic actuator 506, a field is produced which attracts the iron surface 510 toward the electromagnetic actuator 506. The flexible pivot arm 518 bends and applies a restraining force against the movement of the housing 504 toward the electromagnetic actuator 506. By varying the magnetic flux of the electromagnetic actuator 506, the housing 504 can move in an arc across the plane of the microfluidic chip 502, allowing for detecting the center of the channel as a result of the change in signal resulting from the light emanating from the channel. A position resolver 524 confronts surface 526, where the position resolver 524 detects the position of the housing 504. The position resolver 524 may determine the distance between it and surface 526 using sound or optics. Once the center of the channel has been determined by a data analyzer, the signal from the position resolver 524 related to the position of the housing 504 directing light to the center of the channel can be recorded and the housing 504 restored to that position for each determination in that channel. In this manner one need not scan the surface each time one wishes to have a determination, but may rely on the signal from the position resolver 524 to determine when the housing is properly positioned.

In the next two figures, the housing is mounted on a carrier which moves in a plane parallel to the surface of the microfluidic chip, so that the light incident from the housing may be in the same direction onto the microfluidic chip.

Figure 6:
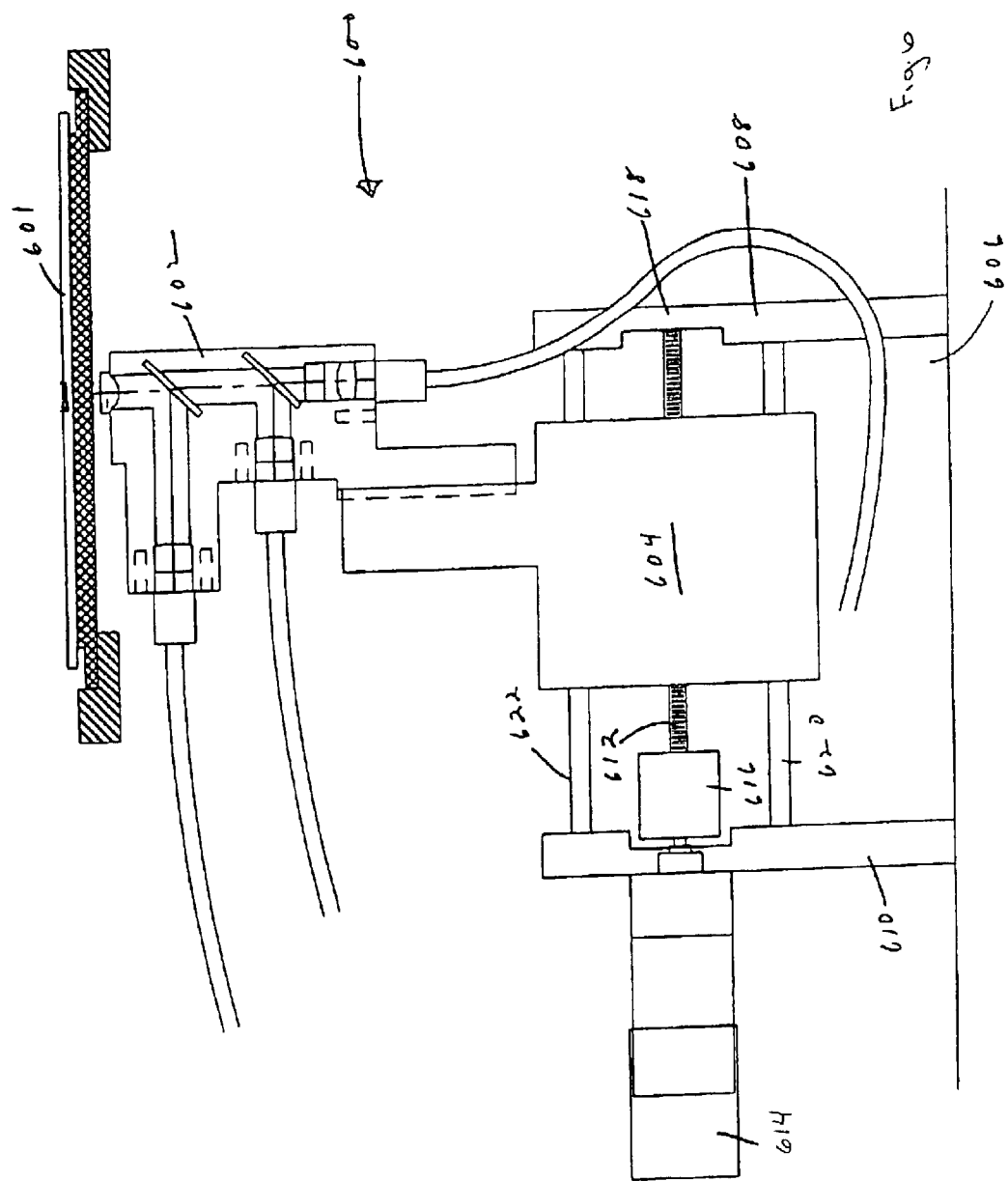
FIG. 6 is an elevational view of an alternative embodiment using a mechanically moved carrier in a plane parallel to the microfluidic substrate for orienting the optical detection system.

In FIG. 6, the device 600 has a microfluidic chip 601 under optical system 602 mounted on movable carrier 604. Movable carrier 604 is mounted on stand 606, which has two confronting support posts 608 and 610, respectively. The movement of movable carrier 604 is controlled by lead screw 612 which passes through a threaded channel in movable carrier and is turned by motor 614 connected to lead screw 612 by coupler 616. Lead screw 612 is supported in post 608 by bearing 618. Two guide shafts 620 and 622 extend between posts 608 and 610 and pass through smooth channels in movable carrier 604 to maintain the movement of movable carrier 604 in the same plane. The motor 614 is controlled by a data analyzer, which controls the movement of movable carrier 604 and receives signals from optical system 602. When the center of the channel is detected, the movement of the movable carrier is stopped and maintained in the same position.

Figure 7:
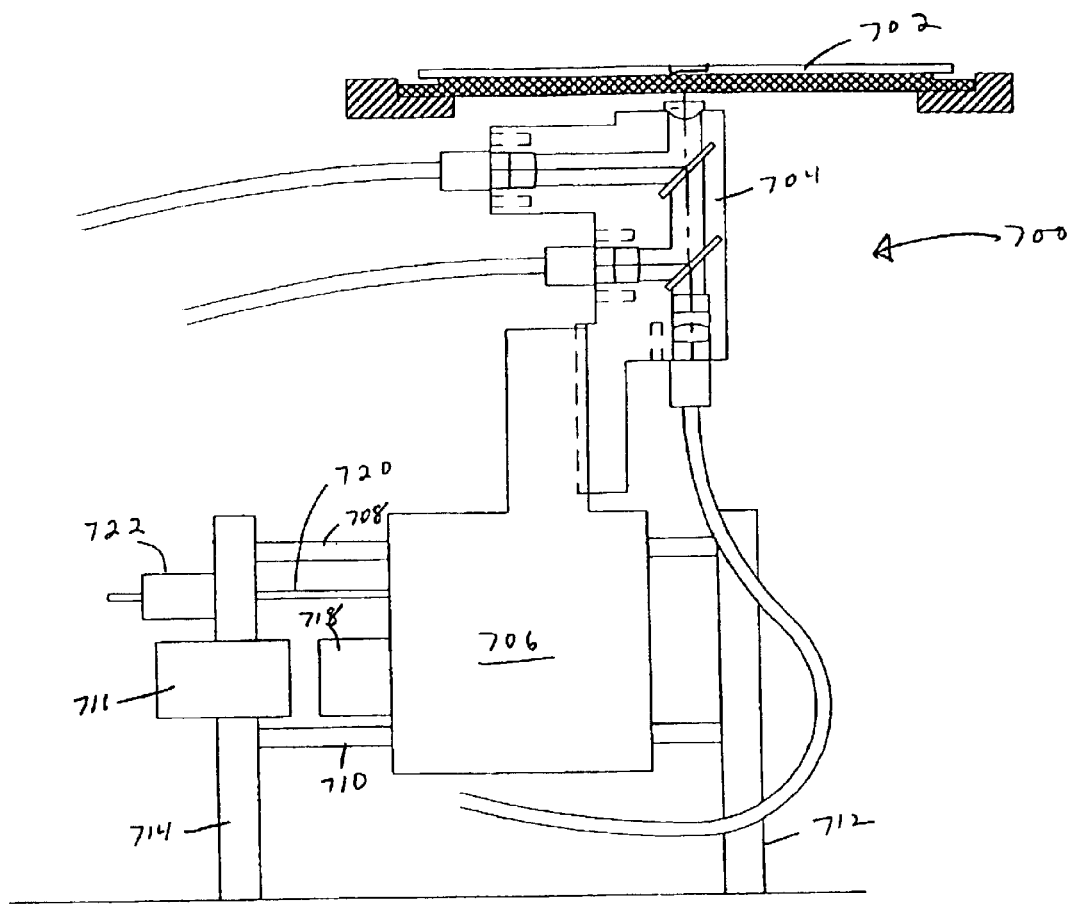
FIG. 7 is an elevational view of an alternative embodiment of using an electromagnetic actuator for moving a carrier in a plane parallel to the microfluidic substrate for orienting the optical detection system.

In FIG. 7, the device 700 uses an electromagnetic actuator for controlling the movement of the optical system. In order to maintain the optical system in a linear plane parallel to the surface of the microfluidic chip, one uses one or more linear guides, such as a guide shaft, guide bearing, etc. The device 700 has microfluidic chip 702 and optical system 704 which is mounted on movable carrier 706. As in FIG. 6, movable carrier 706 is guided by guide shafts 708 and 710, which extend between the posts 712 and 714 and pass through smooth channels in movable carrier 706 to maintain the travel of movable carrier 706 in a constant plane parallel to the upper surface of the microfluidic chip 702. Mounted on post 714 is electromagnetic actuator 716. Mounted on the side of movable carrier 706 confronting electromagnetic actuator 716 is bar magnet 718. By varying the strength and polarity of the field of electromagnetic actuator 716, the movable carrier 706 can be moved back and forth along the guide shafts 708 and 710. A detection rod 720 is attached at one of its ends to movable carrier 706 and extends through post 714 and position resolver 722. The detection rod 720 is position coded, such as a graduated change in color, transparency, reflectivity, or the like, so that the portion of the detection rod 720 in the position resolver 722 may be accurately determined. Once the appropriate position of the detection rod 720 is determined, the movable carrier 706 can be brought back to the same site for further monitoring of the channel in the microfluidic chip 702. By having signals from the optical system 704 sent to a data analyzer which also monitors the position of the detection rod 720, the center of the channel in the microfluidic chip can be related to the position of the detection rod 720, when the optical system is situated at the center of the channel.

Figure 8A:
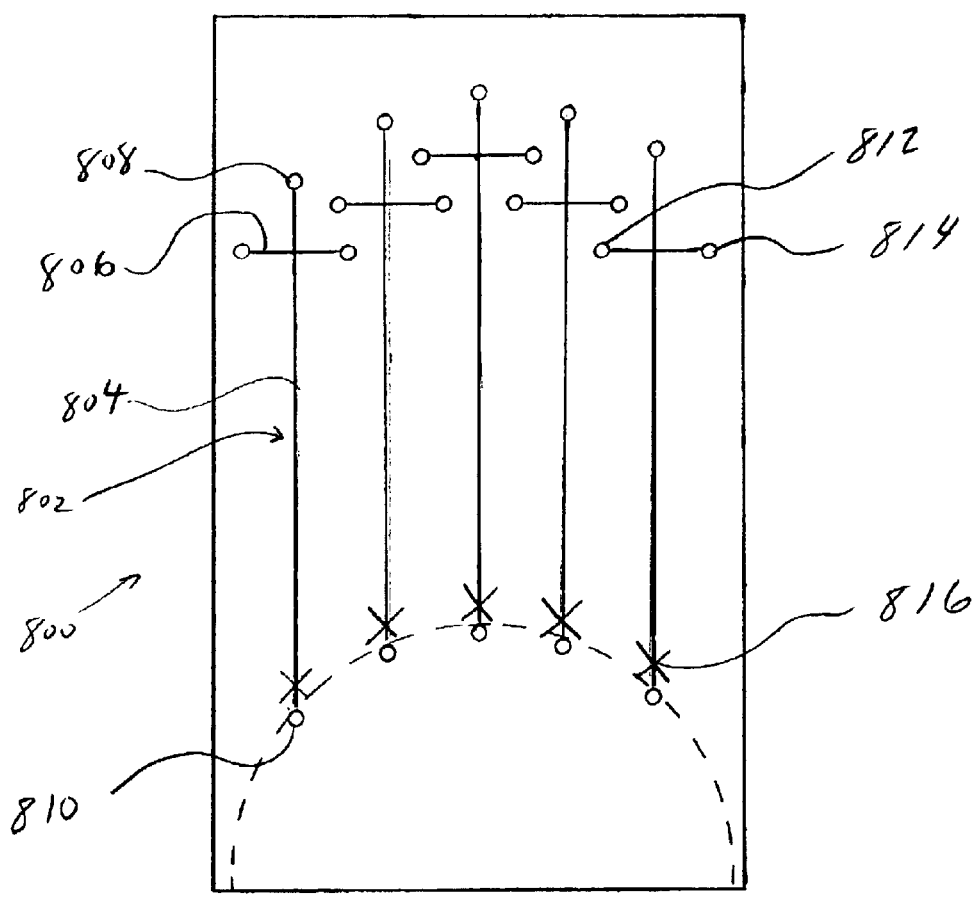
FIG. 8A is a top view of the surface of a microfluidic chip in which a plurality of channel networks are featured.
Figure 8B:
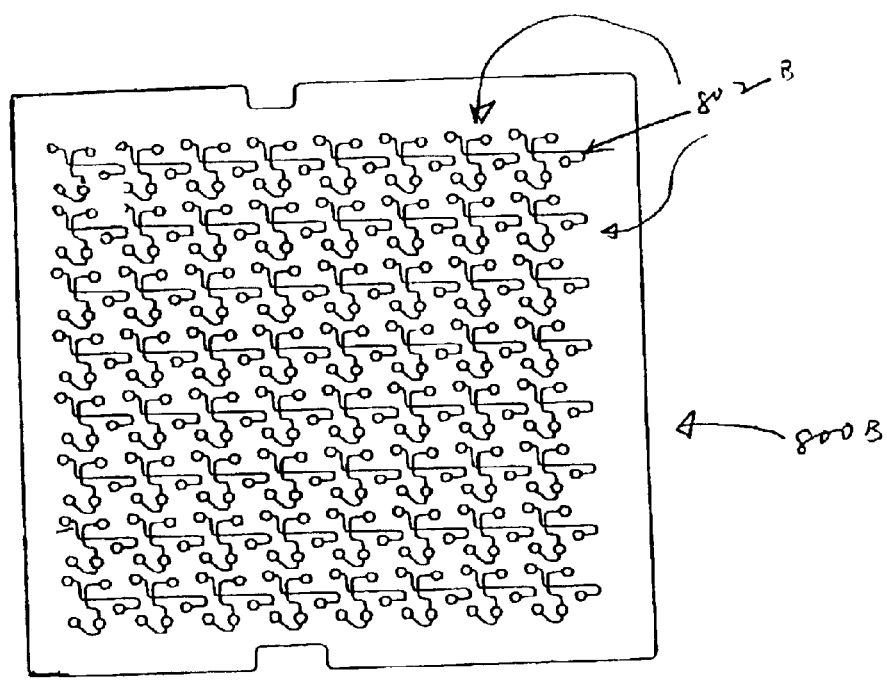
FIG. 8B is a top view of the surface of another microfluidic chip in which a plurality of channel networks are featured.

As previously indicated, the channels may take many patterns in a microfluidic chip. FIG. 8A shows a diagrammatic top view of the surface of a microfluidic chip 800. A plurality of channel networks 802 have main channel 804, cross-channel 806 with ports and reservoirs 808 and 810 for the main channel 804 and ports and reservoirs 812 and 814 for the cross-channel 806. The channel networks 802 are spaced apart in an arc and the "X"s 816 indicate the detection sites on the main channels 804 at which the optical housing is positioned. The spacing between the channels may be at least about 0.25 mm. Instead of an arc, the channel networks could be distributed to define a circle, where the optical housings could be mounted on a platform, which allows a group of the housings to rotate to address different groups of channel networks. FIG. 8B illustrates another chip 800B having a plurality of channel networks 802B.

If desired, various electrode patterns may be made part of the microfluidic chip, which may be connected to a computer or other data analyzing device, which serves to control the voltages at the various electrodes during the course of the operation. In addition, the computer may serve to control the optical detection device positioning during the operation.

Submersible Light-Directing Members

Figure 8C:
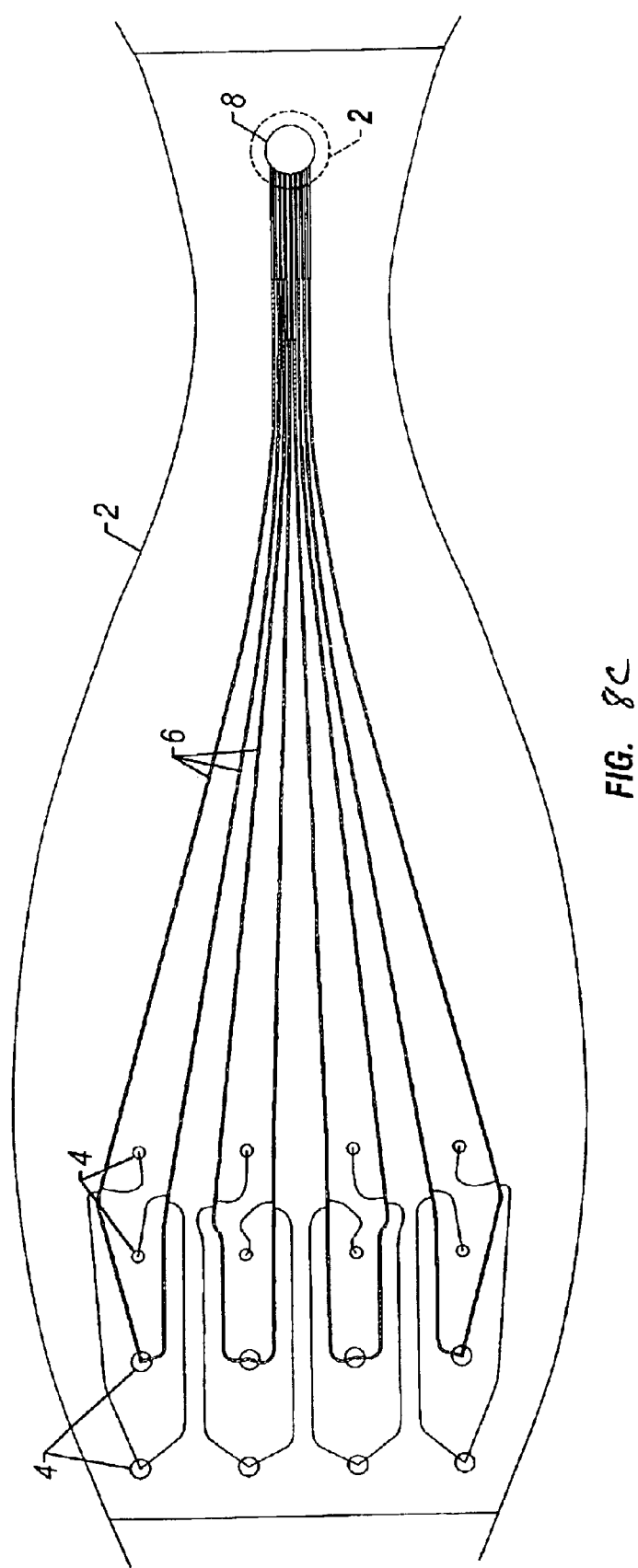
FIG. 8C is a top view of another channel network of a microfluidic chip.
Figure 9:
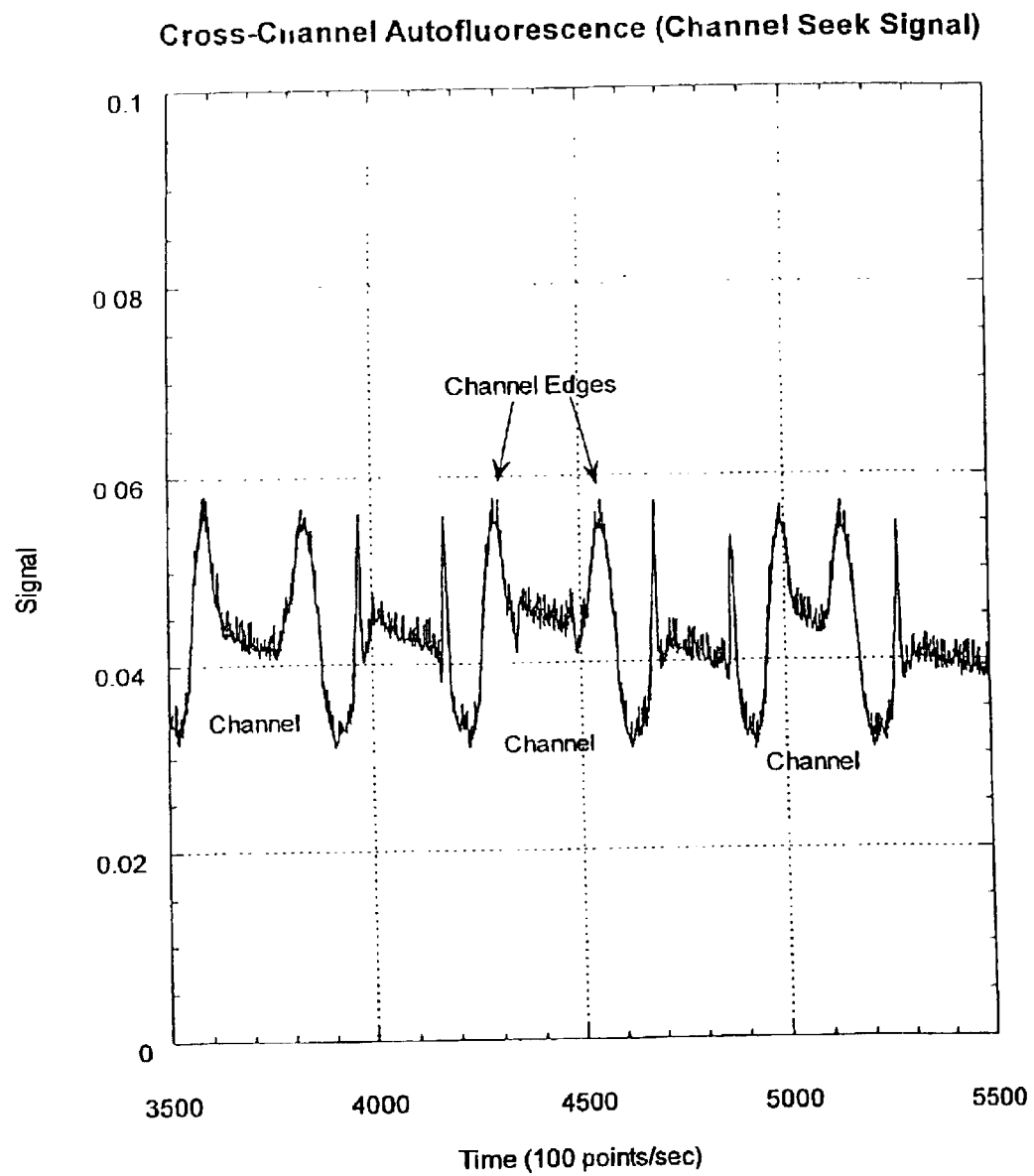
FIG. 9 is a graph of the observed signal when orienting the optical system in relation to a channel. The conditions under which the determination was run are: laser power 2 mW; spot size 10 $\mu$m at FWHM; acrylic microfluidic chip, 30 $\mu$m deep channel, 80 $\mu$m wide filled with HEPES buffer (50 mM, pH 7.4); scan across open channel (back and forth) at approx. 400 $\mu$m/sec; Mini-Confocal Optical System with 488 nm excitation (Argon-Ion laser), 530 nm emission filter, 30 nm FWHM bandpass; and focus nominally set for optimum signal performance.

The above described detection system may also be used in combination with a light-directing member fixed on the microfluidic device to direct light at a fluorescent sample. The light-directing member is configured to direct light from the light source axially through a channel such that the light beam avoids illuminating the side walls of the channel. Consequently, when light is collected from the segment of the channel or detection volume holding the fluorescent sample, little or no autofluorescence is detected. An example of a microfluidic device which may be used in combination with such a light directing member is shown in FIG. 8C. Examples of light-directing members are shown in FIGS. 10 to 17B.

Figure 10:
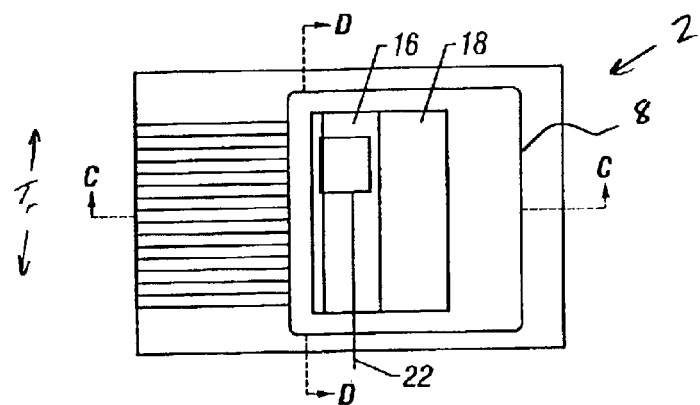
FIG. 10 shows the features of the well together with light-directing hardware.
Figure 11:
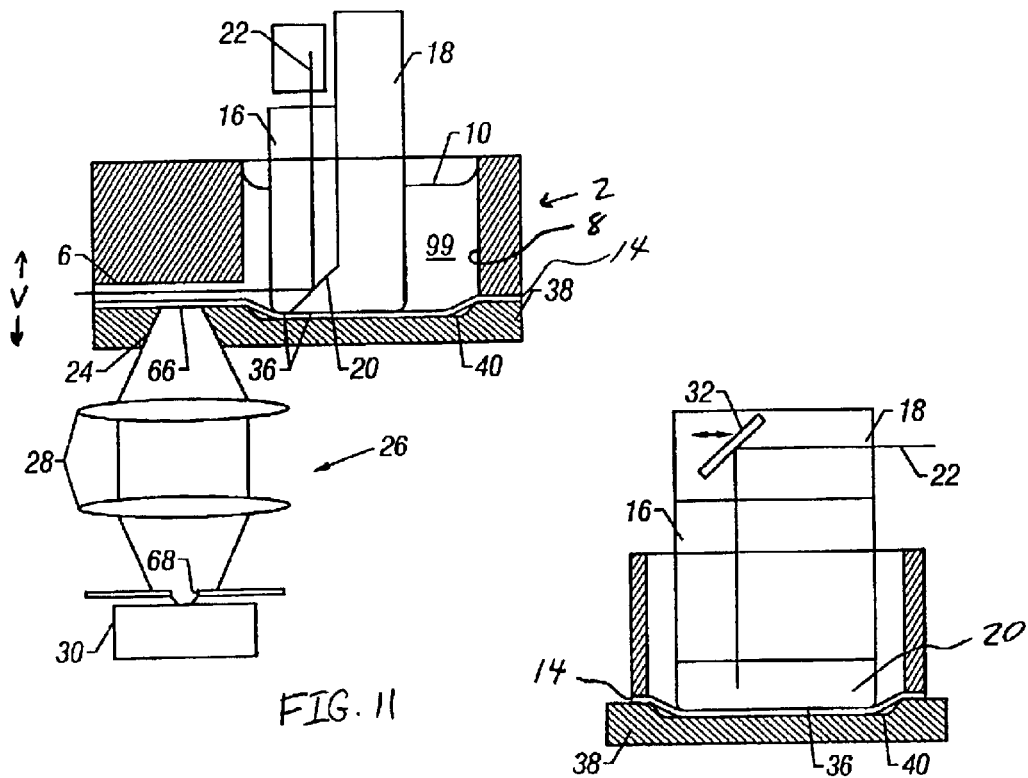
FIG. 11 is a cross-sectional view of FIG. 10 taken along line C—C.
Figure 12:
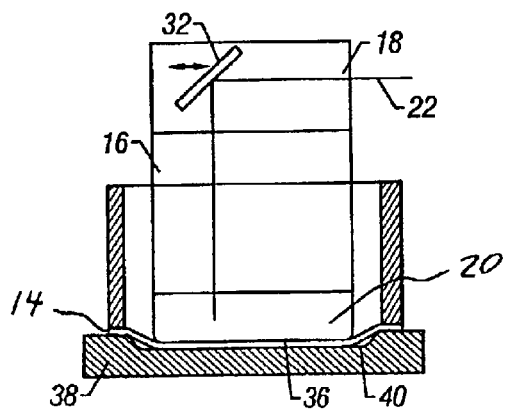
FIG. 12 is a cross-sectional view of FIG. 10 taken along line D—D.

Turning now to FIG. 10, a top view of a microfluidic device 2 having a light-directing member 16 in a well 8 is shown. FIGS. 11 and 12 show side and end views taken along lines C—C and D—D, in FIG. 10. In each, optional prism 16 is backed by an optional support member 18. A reflecting surface 20 is provided. As shown in FIG. 11, these components may be submersed in media 99. Media 99 is contained in the chip. Examples of a media include but are not limited to polyacrylamide or agarose gels, and buffered solutions.

Reflecting surface 20 may be provided in connection with prism 16 or support member 18. It may be provided in connection with prism 16 by way of a reflective coating deposited on the angled surface of the prism. The coating chosen should be selected so as to reflect a beam of sufficient intensity to carry out the detection methodology described below. Accordingly, it may be preferred to use aluminum or silver coatings over gold since they absorb a lower percentage of the wavelengths of light produced by such lasers as typically used in detection schemes. However, for other reasons discussed below, it may be more important to utilize a less corrosive material such as gold or platinum for reflecting surface 20. In any event, the material coating may be applied by electro-plating, sputter coating or otherwise as would be known to one with skill in the art.

Also, the reflecting surface may be a polished portion of the light-directing member. In one variation, the light-directing member is chromium carbide and a portion of the distal end of the light-directing member is polished to form the reflecting surface. This construction thus may provide both reflectance and, if desired, conductance to electrokinetically transport fluids within the channels as discussed herein.

A reflective coating may be applied to the outside of prism 16 or on support 18. If both a support and a prism is to be used, a transparent seal (such as provided by epoxy) may be preferred between the parts if the reflecting surface is to be provided on support 18. Passing light through a prism offers an advantage in that it avoids passing light through media contained in a well or reservoir. Accordingly, loss of beam light intensity and fluorescence interaction with this material is avoided. Moreover, passing light though meniscus 10 will not occur, thereby avoiding any lens-type effect this has on beam 22 increasing the difficulty in which it may be directed down the length of fine channels. Indeed, it is for reason of beam divergence that a laser is the most preferred source of light for the invention. The coherent beam offered by such a device allows for greater light intensity as a point of interest for a given distance the light most travels. An alternative method for delivering light to a desired location involves inserting a fiber optic within the well or channel in an orientation to achieve the desired illumination or excitation.

Regardless of whether a prism is used or not, if the reflective surface is to be provided in connection with support 18, it is possible no coating may be required. Instead a polished surface may suffice, so long as absorption effects of the base metal of support 18 is acceptably low.

When a prism is provided, instead of using a coating on the prism for reflective surface 20, it may be provided by selecting parameters sufficient to result in total internal refraction within prism 16 to redirect a beam of light 22 instead. This phenomena is described by the equation:

$$\sin \theta_c = n_2/n_1 \text{ (for } n_1 > n_2\text{)}$$

where $\theta_c$ is the minimum angle at which total internal reflection occurs and $n_1$ and $n_2$ are the refractive indices of the material in which total internal reflection is desired and that of the material external to the material within which total internal reflection is desired. Since $n_2$ will approximate the value of water (n=1.33) for most solutions used in well 8, certain design considerations must be taken into account. To utilize a reflection surface angled at 45° relative to the initial beam trajectory, a prism material having a refractive index>1.88 may be used. Accordingly, for such a setup, any one of a number of rare-earth doped glasses may be used. Where a lower refractive index material is desired, such as quartz (n=1.47) or crown glass (n=1.52), the geometry of the prism may be modified, together with mounting structure associated with the light source to accommodate a higher incidence angle. However, a 45° angle of incidence is preferred in each variation of the invention since it turns a beam by 90°, allowing associated hardware to be setup at orthogonal angles.

However provided, in the variation in FIGS. 10 to 12, reflecting surface 20 is oriented to reflect a beam 22 along a channel 6 as shown in FIG. 11. In so doing, sample material within channel 6 at and above a detection window 24 is illuminated. This in turn causes tagged, labeled or marked material to fluoresce producing light that may be picked up by a detection system 26. To increase signal and enhance illumination, the sample detection channel may also incorporate certain surface coatings or claddings, or be composed of specific materials such that the channel walls can serve as a waveguide reflecting beam 22 inward. Various detection systems may be employed. For example, a system utilizing one or more lenses and a PMT device or a CCD camera 30 may be employed.

A suitable light collection setup is shown in FIG. 11. In this case, light is collected through lenses 28 from the bottom of the card or chip. The light is imaged through a slit 68 and collected by, for example, a PMT. The slit provides a spatial mask thereby setting the size of a detection region 66. The amount of fluorescent light that is collected from the bottom of the card may thus be controlled by the presence and size of the slit 68. In this manner, an optimum amount of fluorescent light may be collected. Alternatively, sets of pinholes and other variations can be utilized for the mask configurations disclosed herein.

It is also contemplated that slit 68 may be positioned on top of or on the bottom of backing 14. The slit may be, for example, a layer inside the chip or a layer formed on an outside surface. The slit may also be in the form of a coating deposited on the cover film or backing 14. While the present invention may be utilized to direct a beam up a single channel or trench, it is preferred that provision be made to allow detection in multiple channels running more-or-less simultaneously. This may be accomplished using multiple beams, each aligned to reflect into a given channel. Also, it may be accomplished by scanning a single beam into a number of channels (or simply directing it across a number of channels). A single beam may be provided normal or transversely to a region of parallel channels or channel streams similar to the configurations disclosed in U.S. Pat. Nos. 5,833,826 and 5,741,412, and WO 01/20309. Additional ways of beam scanning are contemplated, the first of which is most clearly shown in connection with FIG. 12. Here, a mirror 32 to be attached to structure under control enabling it to traverse the face of reflecting surface 20 as indicated is provided. Of course, it is contemplated that mirror 32 and its source may be oriented otherwise. Also, in the case that the detection path is mounted on a scanning head, the PMT may be part of the head. However, the PMT or detector may also be remotely mounted in a fixed location and connected to the head with a fiberoptic.

An example of a linear control mechanism for moving the mirror is a voice-coil actuator. Also, other types of actuators and devices may be used to move the mirror relative to the reflecting surface 20 as is known to those of ordinary skill in the art. Feedback control systems may also be incorporated into the system to optimize the position of the mirror 32 relative to the reflecting surface 20.

FIGS. 13, 14A and 14B illustrate other manners in which to scan a beam into multiple channels. FIG. 13 shows a channel configuration with a prism 16 located at the center of a waste well 13. In FIG. 13, channels 6 empty into waste well 13 so each has an axis through a center point shared by prism 16. A circular waste well for such a configuration is preferred, but not required. FIGS. 14A and 14B show alternate side views of the prism in FIG. 13.

The prism configuration in FIG. 14A includes a planar reflecting surface 20. The backside 34 of the reflecting surface may be filled in as shown. Alternately, it may be left open. It is advantageously filled in by material such as epoxy to protect any coating on reflecting surface from corrosive interaction with material in well 13. Also, it provides for a cylindrical body. This may be useful since prism 16 in FIG. 14A is preferably placed in well 13 and rotated in order to direct beam 22 into each channel 6 to enable detection when multiple channels are used in parallel. Rotating a cylindrical body rather than one missing a section of material produces less disruption of material within well 13.

The reflecting surface associated with prism in FIG. 14B is configured differently although backspace 34 may, likewise, be filled in with material. This will similarly insulate reflecting surface 20. However, to effect scanning a beam into multiple channels with the inventive variation in FIG. 14B, the beam is rotated instead of the prism. It may be preferred that the conical reflecting surface 34 be faceted in order to avoid divergence of beam 22.

For the variation in FIG. 14B, filling backspace 34 may provide another advantage. Namely, it provides a flat surface at the base of prism 16 useful for positioning reflecting surface 20 with respect to the channels. In order to properly locate reflecting surface to direct a beam up a channel, prism placement can be critical.

Additionally, the reflecting surface 20 and beam 22 may be held fixed relative to one another and the channels may be rotated such that each channel 6 may be aligned with the beam. This may be performed by fixing the prism 16 and the beam 22 and rotating, for example, the microfluidic chip. Rotation of the above mentioned components may be performed in a number of manners including, for example, using a galvanometer-type actuator.

FIGS. 11 and 12 show a manner of accurately and precisely placing reflecting surface 20 to direct a beam as desired. This approach may also be used with the prisms shown in FIGS. 14A and 14B. Referring to FIGS. 11 and 12, a base 36 of a prism, support structure or both abuts a portion of chip 2 maintained as a stable location feature. As shown, backing 14 is maintained in a set location by a platen or fixture 38. Backing or cover 14 is shown bowed or flexed into recesses 40 in platen 38. An advantage of such an approach is that the reflected beam may be directed down the channel 6 within the channel walls. Further, by controlling the point that the beam strikes the reflecting surface 20, the reflected beam may be vertically (V) and transversely (Tr) centered in channel 6 minimizing signal interference arising from light striking the walls of the channel. Another advantage of such an approach is the ability to lower the position of reflecting surface 20 with respect to chip 2 so as to be able to bounce a beam off an area inboard of the leading edge of reflecting surface. Further, it allows passing beam deep within the interior of a prism, if used. It also eliminates the requirement to accurately control card thickness.

For chips where the channels are not at the bottom of structure, but rather formed at an intermediate height within a body, a recessed location-function approach may not be most preferred, or even feasible. Instead, it may be desired to simply locate base 36 against the base of a substantially non-deformable portion of the chip. On the other hand, it may be desirable to locate reflecting surface 20 relative to channels in a chip by way of features other than a base 36. For instance, in connection with the prism arrangement shown in FIG. 14A, base 36 is held so it does not contact chip 2. Instead it rotates above backing 14. Accordingly, stop features incorporated in a holding and actuating mechanism can set the height of reflecting surface 20 relative to the chip. Such an approach may also be used in conjunction with prisms or support members that do not move once placed in relation to a chip. Yet another approach is to locate a reflecting surface by reference to any repeatable feature that may be provided in a chip 2 or chip platen 38.

Especially in connection with the variations of the invention shown in FIGS. 10 to 13, 14A and 14B, an electrode feature may be included with whatever body is submerged in wells 8 or 13. This may be accomplished by utilizing a conductive material for optional support member 18. Stainless steel, or titanium alloy may be desired for corrosion resistance. Alternately, a coating of gold or platinum may be applied to support 18 so it may resist corrosion. Indeed, a suitably electrically conductive coating may itself function as an electrode even if the underlying material of support 18 is not conductive. Similarly, a conductive coating may be applied to prism 16 so at least a portion of the exterior of this member serves as an electrode. Instead, a simple wire or rod electrode may be affixed to whatever structure prism 16 and/or support member 18 is attached to serve as an electrode for driving chip 2.

Hydrophilic coatings may be applied to prism 16 and/or support member 18. Hydrophilic coatings may be helpful in, amongst other things, avoiding bubbles.

With any of the systems described herein, it is noted that mounting and actuating structure for the prism or a supporting member for reflecting surface may be provided to advance the reflecting surface into a recess within a chip. Alternately, a chip may be moved in order to submerge a reflecting surface that is mounted in a stationary fashion. Provision of such constructional detail in the form of collateral structure and control for that structure is within the ability of those within the level of ordinary skill in the art.

Figure 15:
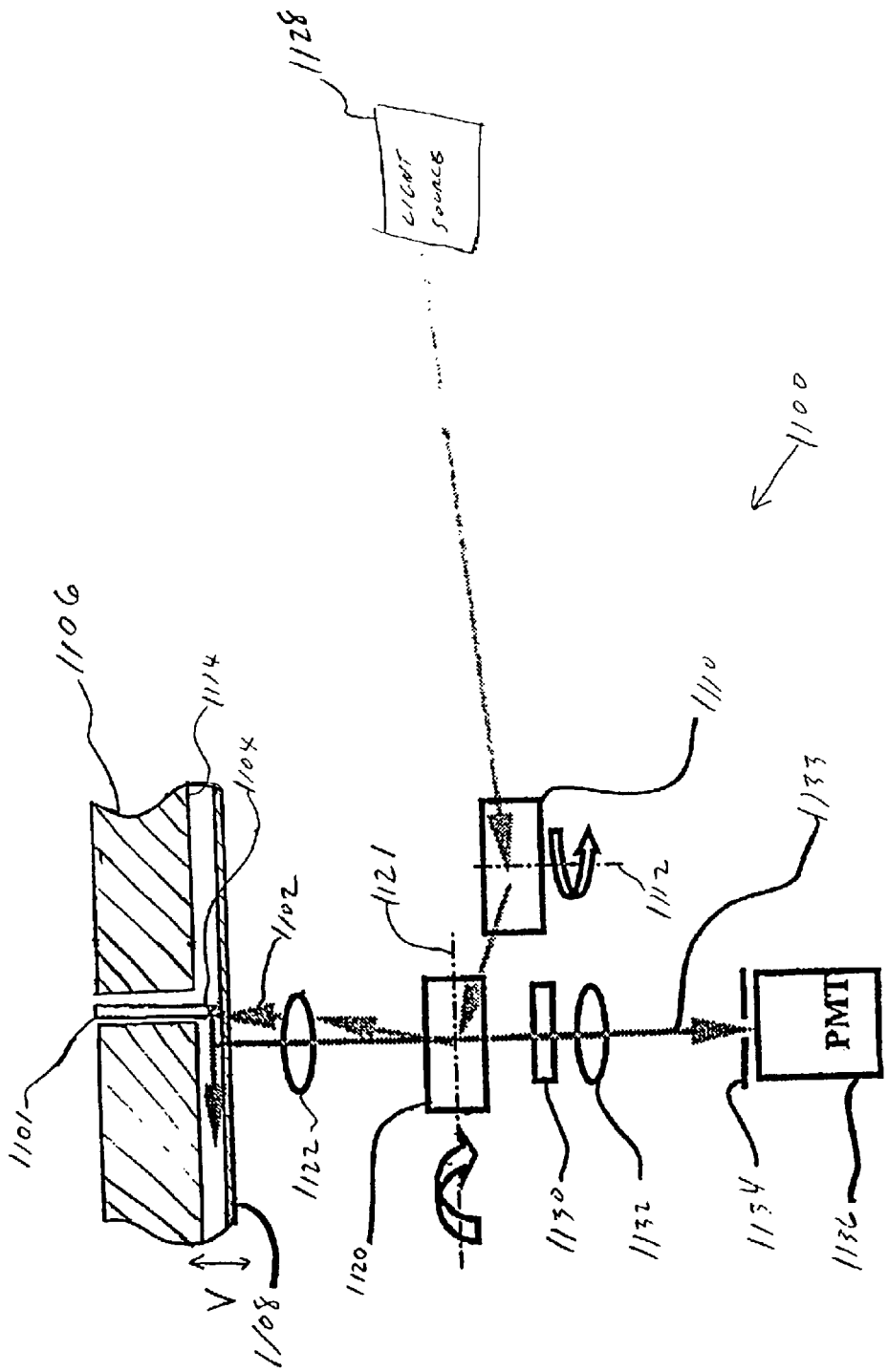
FIG. 15 shows a system including optical hardware and a light-directing member.

FIG. 15 shows another system 1100 for illuminating and detecting sample in a channel of a microfluidic device. The system 1100 shown in FIG. 15 includes a submersible probe or light-directing member 1101. The light-directing member may be positioned in the microfluidic device as shown in FIGS. 15 to 17B such that light may be directed through the backing and off the reflecting surface of the light-directing member to illuminate the sample in the detection zone. The light-directing member 1101 serves to aim light through the channel 1114. Unlike the system shown in FIGS. 10 to 12, however, the excitation beam 1102 of the system shown in FIG. 15 is directed at the reflecting surface 1104 from below the microfluidic chip 1106. The excitation beam 1102 is directed through the backing or cover film 1108 before striking the reflecting surface 1104.

The optical hardware shown in FIG. 15 includes various components such as a light source 1128, a rotatable first mirror 1110, a rotatable second mirror 1120, and lens 1122. Light from the light source 1128 follows an optical path which is adjusted by the above mentioned components to control the point or location that the excitation beam 1102 strikes the reflected surface 1104. By controlling the location that the excitation beam 1102 strikes the reflected surface 1104, the position of the excitation beam within the channel 1114 may be adjusted and axially centered. Vertically (V) centering the excitation beam within the channel 1114 reduces interference with the channel walls.

The optical path of the light may be controlled and adjusted by changing the angle of the first mirror 1110 and second mirror 1120. The first mirror 1110 is rotatable about a first axis 1112 which is perpendicular to channel 1114. The first mirror directs light from the light source 1128 towards the rotatable second mirror 1120. The second mirror is rotatable about a second axis 1121, which is parallel to channel 1114. The second mirror directs light towards an objective lens 1122, which launches the light towards the reflective surface 1104. The reflective surface 1104 makes an angle with the channel 1114 which may range from 10° to 80°, more desirably about 45°. The angle should be selected such that the beam can reflect off the reflective surface 1104 down channel 1114. In this manner, beam 1102 illuminates or excites materials in channel 1114. Preferably, the reflected light is directed along the channel's central axis or midway between opposing walls defining the channel.

As stated above, the system 1100 is adapted to adjust and control the position of the light beam through the channel 1114. In particular, vertical (V) control of the light beam in the channel 1114 is provided by adjusting the angle of the first mirror 1110. When the first mirror is rotated about the first axis, the beam follows the above described optical path and strikes the reflecting surface at a point corresponding to the angle of the first mirror. Accordingly, the light reflected into and through the channel 1114 may be vertically adjusted by changing the angle of the first mirror about the first axis.

Various apparatuses may be used to move or rotate the mirrors. An example of a rotational actuator to rotate the first mirror is a galvanometer. To reiterate, it is desirable to direct the reflected beam through the vertical center of the channel or midway between the cover film and the channel walls to reduce background and interference. Providing a black card or body also serves to reduce background noise and cross talk.

The excitation beam may also be adjusted in the transverse direction. As shown in FIG. 15, the second mirror 1120 is rotatable about a second axis 1121. The second axis 1121 is parallel to channel 1114 and thus when the second mirror is rotated the excitation beam 1102 is directed towards a different target region of the microfluidic device. This transverse adjustment or resolution may be as small 1 to 10 μm or less. Also, in the case where several parallel channels fluidly connect with one waste well, the second mirror may enable the beam to sequentially illuminate each channel. Additionally, the second mirror may be rotated to adjust (or step) the beam greater distances up to, for example, ±3.5 mm or more.

In another variation, a lens having a larger field of view such as a telecentric lens may be used in combination with the above described mirrors. Consequently, the light beam may be stepped across greater distances on the chip. For example, light from such a lens may be directed at second light-directing members disposed in second waste wells of a second functional unit on the microfluidic device.

Various apparatuses may be used to move or rotate the second mirror. The second mirror may be held by a rotational actuator such as, for example, a galvanometer. However, other mechanisms may be utilized to rotate or otherwise move the mirrors in accordance with the present invention as is known to those of ordinary skill in the art.

The light beam diameter and the lens may also be selected to provide a beam waist that does not contact the card body or the cover film, thus reducing background fluorescence. For example, the lens may be a 10× objective microscope lens. The lens may have, for example, a numerical aperture of at least 0.45. An example of a beam waist may be 20 μm. However, the beam may be otherwise designed and still be in accordance with the present invention. Again, it is desirable that the beam does not contact the walls of the card or the cover film.

The system shown in FIG. 15 also includes light collecting hardware. The collecting or detecting hardware includes a filter 1130, a second lens 1132, a slit 1134 and a PMT 1136. The first lens 1122 collects light emitted from a fluorescing sample in the detection zone or segment of the channel. The emitted light is directed to and through second mirror 1120. The second mirror in this construct may be a dichroic mirror such that the light may pass through the second mirror 1120. The filter 1130 excludes certain wavelength ranges which are not of interest. The emitted light beam is then focused using a lens 1132 into a slit 1134. Finally, a photomultiplier tube 1136 is shown receiving the collected light beam 1133. The photomultiplier tube 1136 may provide a signal corresponding to the concentration of analyte, for example.

Figure 16A:
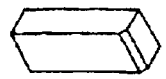
FIGS. 16A and 16D show various views of a light-directing member.
Figure 16B:
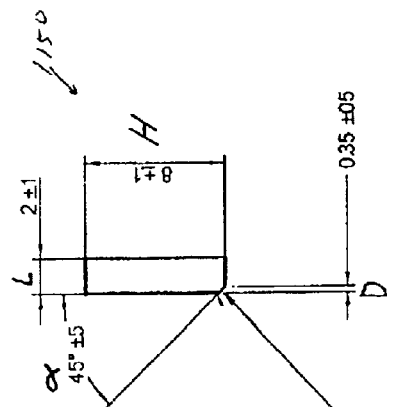
Figure 16C:
Figure 16D:
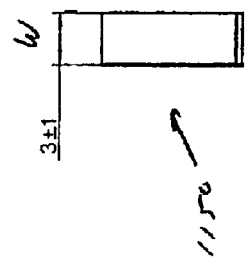

FIGS. 16A to 16D show details of a reflective probe 1150, which may be inserted into a waste well or other well to reflect the excitation beam in accordance with the present invention. FIG. 16A shows a perspective view of the reflective probe 1150. The probe may be made, for example, from chromium carbide with a diamond machined 45° mirror reflecting surface 1152. This construction may also provide, if desired, an electrical conductor to electrokinetically drive fluids from one location to another within the channel network.

Additionally, the reflecting surface may have other angles so long as the excitation beam is reflected into the detection zone properly. Preferably, the beam does not interact or hit the walls of the channel prior to illuminating the material to be excited. Also, cross talk between channels is undesirable as each of these phenomena decreases sensitivity of the detection system.

The construction of the chip itself can also reduce cross talk and increase sensitivity. For example, a chip may be made from black or opaque material, which exhibits little background fluorescence. Such a configuration is relatively easy to manufacture. The chip may be molded, for example, using a black material or resin. Also, the cover film enclosing the channels desirably has a low fluorescence.

Referring to FIGS. 16A to 16D, the reflective probe 1150 may have a generally elongated shape with a reflective surface 1152 adjacent the distal end. The height (H) of the probe may range from 5 to 20 mm and perhaps, 5 to 10 mm. A desirable height may be 8±1 mm. The width (W) and length (L) may also vary. The width and length may be, for example, 2 and 3 mm respectively. Additionally, the dimension (D) for the reflective surface may range from 100 to 300 μm, and perhaps from 0.1 to 1 mm. In the probe shown in FIG. 16B, however, the dimension D is about 0.35±0.05 mm. However, these dimensions may vary and the dimensions of the probe may be selected such that the probe fits within a well of a microfluidic chip.

Figure 17A:
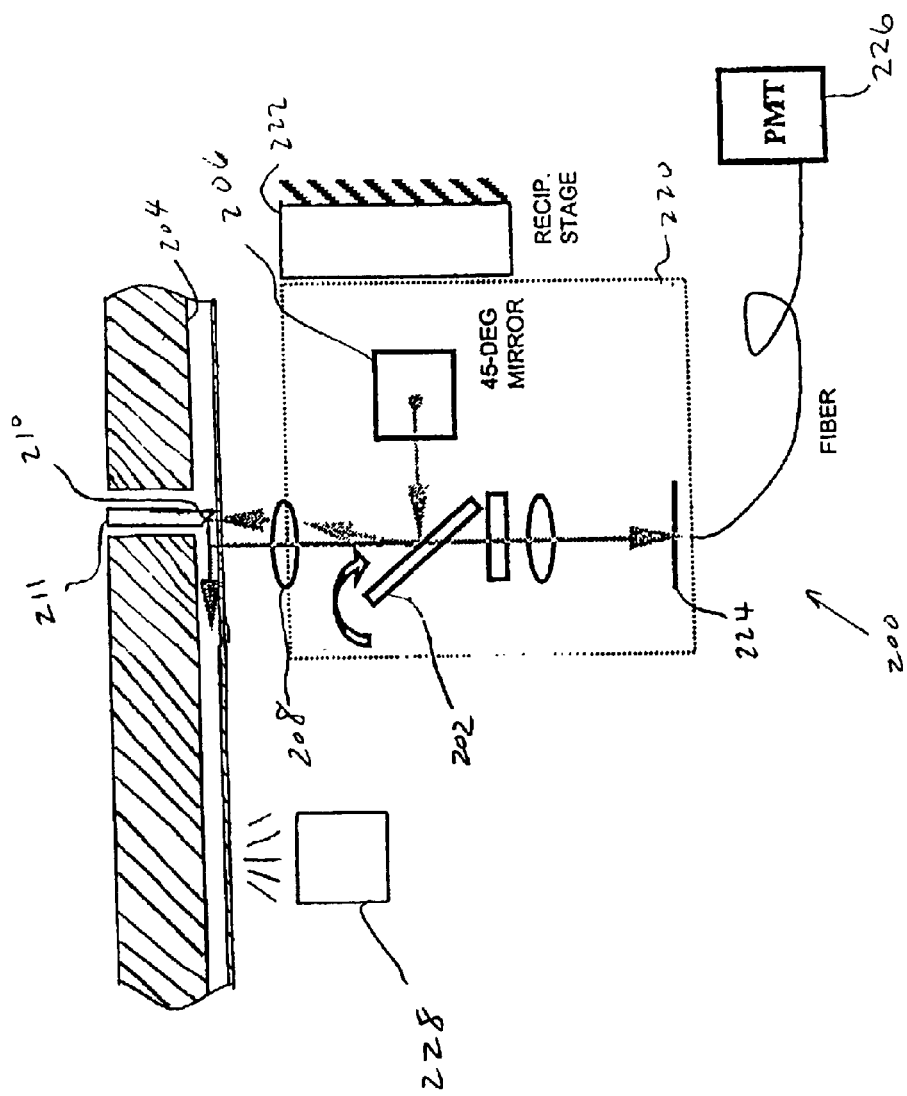
FIG. 17A is a front view of a system having a linearly movable stage to assist in directing light to a target region on a microfluidic device.
Figure 17B:
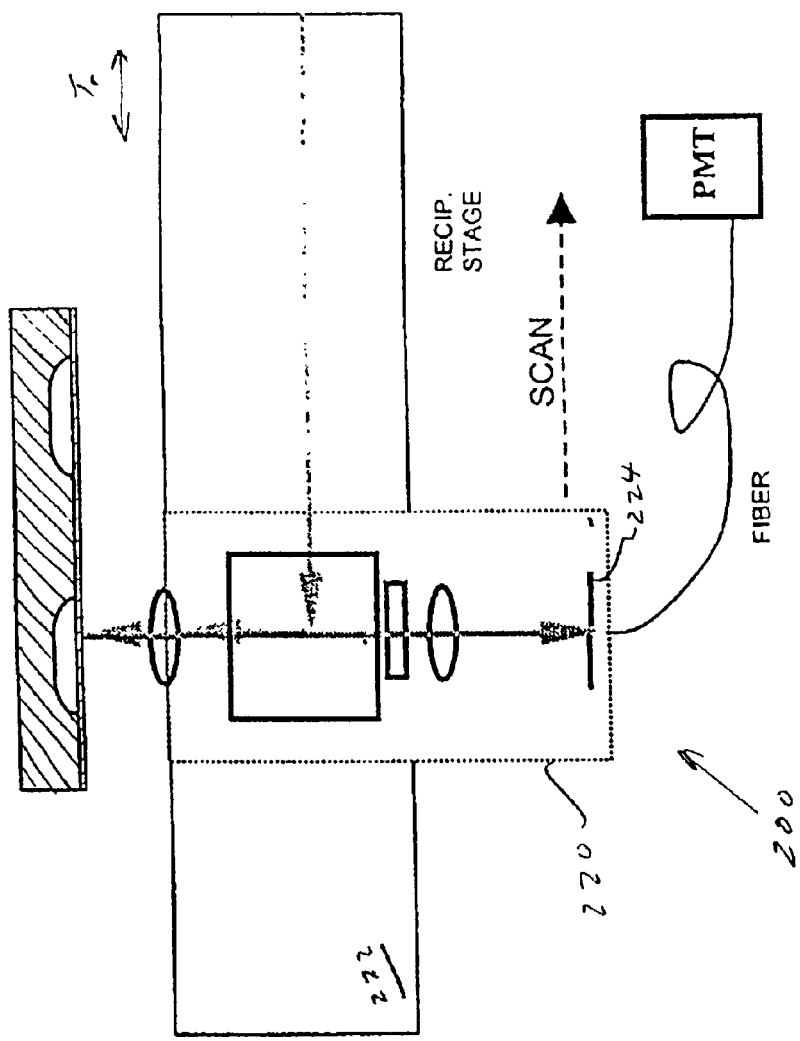
FIG. 17B is a side view of the system shown in FIG. 17A.

FIGS. 17A and 17B are side and front views respectively of another illumination and detection system 200. The illumination and detection system shown in FIGS. 17A and 17B includes a rotatable dichroic mirror 202 which serves to adjust the position of the beam in the vertical direction within a channel 204. In particular, the light beam is reflected off fixed mirror 206 towards rotatable mirror 202. The rotatable mirror 202 may be rotated to change the direction of the excitation beam. Lens 208 receives light from the mirror 202 and launches light towards a point on the reflective surface 210 of light-directing member 211. Thus, when the rotatable mirror 202 is rotated, the point that the beam strikes the reflective surface 210 is moved a distance corresponding to the angle of the mirror 202. In this manner, the beam may be vertically positioned midway between the cover film and the opposing channel wall. As discussed above, it is desirable to position the beam in the vertical center of the channel to reduce background noise arising from light hitting the walls of the channel.

The illumination and detection system shown in FIGS. 17A and 17B also includes a movable optical head 220, which is adapted to move linearly along stage 222. The head 220 moves in the transverse direction (Tr) relative to the channel 204 and thus, by moving the head along the stage, the beam may be aimed at various locations along the width of a channel as well as be aimed at different channels.

Collecting emitted light from the channels may be carried out as described above with respect to the other embodiments of the present invention. Also, an optical fiber may be added between slit 224 and the photomultiplier tube 226. This allows for the PMT or other detecting apparatuses to be separated or divorced from the optical head. Also, when an optical fiber is used, the optical fiber can be sized to emulate a pinhole or slit, eliminating the need for a separate slit part.

Also shown in FIG. 17A is a scatter detector 228 which serves to detect scattered light in the channel. Examples of scatter detectors include PMT's, CCD's, pin diodes and other types of devices which can detect scattered light. The scatter detector in this example is separate from the optical head 220. However, the scatter detector may be mounted to the optical head 220 or otherwise incorporated into the optics of the head. As discussed above, detection of scattered light may be used to adjust the position of the optical head such that the excitation light irradiates the center of the detection zone or channel.

As described previously, the microfluidic device may have a plurality of channels, where depending on the number of channels, all of the channels may be simultaneously addressed by an equal number of optical detection devices or a portion of the number of channels may be addressed at any one time and the optical detection device or microfluidic chip or both moved in relation to each other to permit the optical detection device to address a plurality of different channels. For example, with a microfluidic chip which has 96 channels, each port intended to receive a sample from a well of a 96 microtiter well plate, one may have 8 or 12 optical detection devices in a unit to monitor an equal number of channels. After monitoring an equal number of channels, the optical detection device unit and/or microfluidic chip would then be moved to address a different set of channels and the procedure repeated until all of the channels had been monitored. Accordingly, the moveable optical train may be configured to scan across one channel or it may be configured to scan across multiple channels.

It is evident from the above results that the subject invention provides for an improved manner of detecting fluorophores in microchannels. The device and methods greatly enhance the signal, as well as the signal-to-noise ratio, and permit rapid determination of a large number of samples, so that at a single time numerous channels may be monitored. The mechanisms employed can be miniaturized, so as to be compact, while being able to address a plurality of microchannels in a small space. Various designs of channels are compatible with the detection system.

Although the foregoing invention has been described in some detail by way of illustration and example for purposes of clarity of understanding, it may be readily apparent to those of ordinary skill in the art in light of the teachings of this invention that certain changes and modifications may be made thereto without departing from the spirit or scope of the appended claims.

What is claimed is:

1. An optical detection and orientation system for irradiating a fluorescent sample in a detection volume of a microchannel, wherein said microchannel is in a solid substrate, said system comprising:
    a movable optical train comprising a source of excitation light and an optical element for directing said light at said detection volume;
    a detector for receiving light emanating from said detection volume and transferring said emanating light for analysis; and
    a carrier for moving said optical train and excitation light across the surface of said solid substrate comprising said microchannel in response to changes in light emanating from said detection volume.

2. An optical detection and orientation system according to claim 1, wherein said detector is part of said movable optical train.

3. An optical detection and orientation system according to claim 1, wherein said movable optical train is adapted to scan across the surface of said solid substrate having a plurality of microchannels.

4. An optical detection and orientation system according to claim 1, wherein said movable optical train is adapted to scan across at least eight microchannels.

5. An optical detection and orientation system according to claim 3, wherein spacing between adjacent microchannels is between 0.1 and 1 mm.

6. An optical detection and orientation system according to claim 3, wherein spacing between adjacent microchannels is between 0.2 and 0.3 mm.

7. An optical detection and orientation system according to claim 1, wherein said emanating light comprises fluorescent light.

8. An optical detection and orientation system according to claim 1, wherein said emanating light comprises scattered light.

9. An optical detection and orientation system according to claim 1, wherein said light source is selected from the group consisting of lamp, LED, laser, and laser diode.

10. An optical detection and orientation system according to claim 9, wherein said light source is a laser.

11. An optical detection and orientation system according to claim 1, comprising a plurality of light sources.

12. An optical detection and orientation system according to claim 11, wherein each light source of said plurality of light sources emits light of a different wavelength.

13. An optical detection and orientation system according to claim 1, wherein said light source is a multiple wavelength light source.

14. An optical detection and orientation system according to claim 1, wherein said light source is adapted to provide an expanded beam of light.

15. An optical detection and orientation system according to claim 1, wherein said excitation light is expanded such that a beam is formed having a diameter in the range of 2 to 50 mm.

16. An optical detection and orientation system according to claim 14, wherein said excitation light is diverging.

17. An optical detection and orientation system according to claim 14, wherein said excitation light is converging.

18. An optical detection and orientation system according to claim 1, wherein said light source is adapted to provide a fine beam of light.

19. An optical detection and orientation system according to claim 18, wherein said emanating light comprises scattered light arising from said solid substrate and fluorescent light arising from said sample in said detection volume.

20. An optical detection and orientation system according to claim 18, wherein said emanating light comprises scattered light arising from the media container within the channel and fluorescent light arising from said sample in said detection volume.

21. An optical detection and orientation system according to claim 18, wherein said excitation light is converging.

22. An optical detection and orientation system for detecting fluorescence of a sample material in a detection volume of a microchannel wherein said microchannel is in a solid substrate, said system comprising:
    at least one source of excitation light optically coupled to a movable optical train, said optical train comprising at least one optical element configured to direct said excitation light from said at least one source to said detection volume;
    a carrier supporting said optical train, said carrier being adapted to move said optical train relative to said solid substrate;
    at least one optical receiver configured to collect light emanating from said detection volume, and to transfer said emanating light to at least one detector; and
    a data analyzer configured to analyze said emanating light.

23. An optical detection and orientation system according to claim 22, wherein said movable optical train is adapted to scan across the surface of said solid substrate having a plurality of microchannels.

24. An optical detection and orientation system according to claim 23, wherein said movable optical train is adapted to scan across at least eight microchannels.

25. An optical detection and orientation system according to claim 23, wherein spacing between adjacent microchannels is between 0.1 and 1 mm.

26. An optical detection and orientation system according to claim 23, wherein spacing between adjacent microchannels is between 0.2 and 0.3 mm.

27. An optical detection and orientation system according to claim 22, wherein said emanating light comprises fluorescent light.

28. An optical detection and orientation system according to claim 22, wherein said emanating light comprises scattered light.

29. An optical detection and orientation system according to claim 22, wherein said light source is not part of said optical train.

30. An optical detection and orientation system according to claim 22, wherein said at least one light source is optically coupled to said optical train via an optical fiber.

31. An optical detection and orientation system according to claim 22, wherein said emanating light is collimated.

32. An optical detection and orientation system according to claim 22, comprising a plurality of light sources.

33. An optical detection and orientation system according to claim 32, wherein each light source of said plurality of light sources emits light at a different wavelength.

34. An optical detection and orientation system according to claim 33, wherein at least one light source of said plurality of light sources is selected from the group consisting of a lamp, laser, LED, and laser diode.

35. An optical detection and orientation system according to claim 22, wherein said light source is a multiple wavelength light source.

36. An optical detection and orientation system according to claim 22, wherein said at least one light source emits light having a wavelength in the range of 250 to 800 nm.

37. An optical detection and orientation system according to claim 22, wherein said at least one light source emits light at a wavelength of one of 488, 532, and 633 nm.

38. An optical detection and orientation system according to claim 22, wherein said excitation light is collimated.

39. An optical detection and orientation system according to claim 22, wherein excitation light is expanded such that a beam is formed having a diameter in the range of 2 to 50 mm.

40. An optical detection and orientation system according to claim 22, wherein said carrier is adapted to pivot.

41. An optical detection and orientation system according to claim 22, wherein said carrier is adapted to move linearly.

42. An optical detection and orientation system according to claim 22, wherein said excitation light to excite material in said microchannel is in the form of a beam having a diameter ranging from 1 to 100 µm.

43. An optical detection and orientation system according to claim 22, wherein said excitation light impinges off a reflective member positioned in said solid substrate such that the excitation light is directed into the detection volume, said reflective member being separate from said solid substrate.

44. An optical detection and orientation system of claim 43 wherein said reflective member is positioned in a reservoir fluidly connected with said microchannel.

* * * * *